US012709733B2

(12) United States Patent
Zimmer et al.

(10) Patent No.: US 12,709,733 B2
(45) Date of Patent: Aug. 18, 2026

(54) CELL CULTURE MEDIA

(71) Applicant: Merck Patent GmbH, Darmstadt (DE)

(72) Inventors: Aline Zimmer, Darmstadt (DE); Ronja Seibel, Darmstadt (DE); Corinna Schmidt, Darmstadt (DE); Gregor Franz Werner Wille, Buchs (CH); Markus Klaus Robert Fischer, Buchs (CH); Yannick Pierre Rey, Buchs (CH)

(73) Assignee: MERCK PATENT GMBH, Darmstadt (DE)

( * ) Notice: Subject to any disclaimer, the term of this patent is extended or adjusted under 35 U.S.C. 154(b) by 1074 days.

(21) Appl. No.: 17/776,336

(22) PCT Filed: Nov. 11, 2020

(86) PCT No.: PCT/EP2020/081695

§ 371 (c)(1),
(2) Date: May 12, 2022

(87) PCT Pub. No.: WO2021/094341

PCT Pub. Date: May 20, 2021

(65) Prior Publication Data

US 2022/0411748 A1 Dec. 29, 2022

(30) Foreign Application Priority Data

Nov. 14, 2019 (EP) .................................... 19209150

(51) Int. Cl.
*C12N 5/00* (2006.01)
*C12M 1/00* (2006.01)

(52) U.S. Cl.
CPC ........... *C12N 5/0018* (2013.01); *C12M 29/10* (2013.01); *C12N 2500/33* (2013.01); *C12N 2500/60* (2013.01)

(58) Field of Classification Search
CPC ...................................................... C12M 29/10
See application file for complete search history.

(56) References Cited

U.S. PATENT DOCUMENTS

| | | | | |
|---|---|---|---|---|
| 3,450,752 | A * | 6/1969 | Inklaar | A23L 27/215 562/559 |
| 5,780,090 | A | 7/1998 | Frerot et al. | |

(Continued)

FOREIGN PATENT DOCUMENTS

| | | | | |
|---|---|---|---|---|
| EP | 3221446 | B1 * | 8/2024 | C12N 5/0605 |
| WO | 1997010818 | A1 | 3/1997 | |
| WO | 2020208050 | A1 | 10/2020 | |

OTHER PUBLICATIONS

Shih CN, Balish E. New blood culture medium. J Clin Microbiol. Sep. 1977;6(3):249-56. doi: 10.1128/jcm.6.3.249-256.1977. PMID: 332710; PMCID: PMC274748. (Year: 1977).*

(Continued)

*Primary Examiner* — Evelyn Y Pyla
*Assistant Examiner* — Jagamya Vijayaraghavan
(74) *Attorney, Agent, or Firm* — EMD MILLIPORE CORPORATION

(57) ABSTRACT

The present invention relates to cell culture media comprising N-lactoyl derivatives of one or more amino acid. The poor solubility of some amino acids in cell culture media is overcome by substituting them with an N-lactoyl derivative.

10 Claims, 20 Drawing Sheets

(56) References Cited

U.S. PATENT DOCUMENTS

| | | | |
|---|---|---|---|
| 5,939,459 | A | 8/1999 | Katz |
| 5,952,384 | A | 9/1999 | Katz |
| 6,383,810 | B2 | 5/2002 | Fike et al. |
| 6,482,856 | B1 | 11/2002 | Katz |
| 2004/0048347 | A1 | 3/2004 | Lorbert et al. |

OTHER PUBLICATIONS

Sachs JR. Sodium movements in the human red blood cell. J Gen Physiol. Sep. 1970;56(3):322-41. doi: 10.1085/jgp.56.3.322. PMID: 5476387; PMCID: PMC2225963. (Year: 1970).*

N.T. Tayade, et al, Zwitterion to normal formation of L-Alanine in water solvation as an ultrasonic impact from their Gibbs energy barrier: Experiment with different molarities and DFT simulation for few basis sets, Ultrasonics, vol. 127, 2023, ISSN 0041-624X (Year: 2023).*

Dean L. Blood Groups and Red Cell Antigens [Internet]. Bethesda (MD): National Center for Biotechnology Information (US); 2005. Chapter 1, Blood and the cells it contains. Available from: https://www.ncbi.nlm.nih.gov/books/NBK2263/ (Year: 2005).*

Francke MI, van Domburg B, van de Velde D, Hesselink DA, de Winter BCM. The use of freeze-dried blood samples affects the results of a dried blood spot analysis. Clin Biochem. Jun. 2022;104:70-73. doi: 10.1016/j.clinbiochem.2022.03.007. Epub Mar. 25, 2022. PMID: 35346637. (Year: 2022).*

Dulbecco's Modified Eagle Medium (OM EM). https://www.sigmaaldrich.com/—retrieved Jan. 31, 2025 (Year: 2025).*

"Innovative Chemicals for Process Intensification in Cell . . . " Millipore Sigma, Aug. 2018, www.sigmaaldrich.com/deepweb/assets/sigmaaldrich/product/documents/235/588/innovative-chemicals-cellculturemedia-techbrief-tb2564en-ms.pdf. (Year: 2018).*

Gronke, Robert & Gilbert, Alan. (2018). The Search for Process Intensification and Simplification: Alternative Approaches versus Current Platform Processes for Monoclonal Antibodies. 10.1016/B978-0-08-100623-8.00034-7. (Year: 2018).*

Zhao CJ, et al., "Formation of taste-active amino acids, amino acid derivatives and peptides in food fermentations—A review" Food Res Int 2016, 89, pp. 39-47.

Jansen R.S. et al.,"N-lactoyl-amino acids are ubiquitous metabolites that originate from CNDP2-mediated reverse proteolysis of lactate and amino acids" Proc Natl Acad Sci U S A 2015, 112(21), pp. 6601-6606.

Knott M.E. et al., "Metabolic Footprinting of a Clear Cell Renal Cell Carcinoma in Vitro Model for Human Kidney Cancer Detection" J. of proteome research, 2018, 17, pp. 3877-3888.

Sforza S, Cavatorta V, Galaverna G, Dossena A, Marchelli R: Accumulation of non-proteolytic aminoacyl derivatives in Parmigiano-Reggiano cheese during ripening. International Dairy Journal 2009, 19(10):582-587.

Frerot E, Chen T: Identification and quantitation of new glutamic acid derivatives in soy sauce by UPLC/MS/MS. Chem Biodivers 2013, 10(10):1842-1850.

Bielser M. et al., "Perfusion mammalian cell culture for recombinant protein manufacturing—A critical review" Biotechnol Adv. Jul.-Aug. 2018;36(4):1328-1340. doi: 10.1016/j.biotechadv.2018.04.011. Epub May 5, 2018.

Zimmer Aline et al., "Improvement and simplification of fedbatch bioprocesses with a highly soluble phosphotyrosine sodium salt", Journal of Biotechnology, Elsevier, Amsterdam NL, vol. 186,Jul. 9, 2014, pp. 110-118.

Reinhart David et al., "Benchmarking of commercially available CHO cell culture media for antibody production" Applied Microbiology and Biotechnology, Springer Berlin, 2015, vol. 99, No. 11, pp. 4645-4657.

Salazar Andrew et al.,: "Amino acids in the cultivation of mammalian cells", Amino Acids, Springer Verlag, AU, vol. 48, No. 5, Feb. 1, 2016 (Feb. 1, 2016), pp. 1161-1171.

Anonymous: "Merck Millipore is a business of Cell Line Adaptation Media and Feed Screening Cell Bank Generation Media Preparation Cell Culture Performance Evaluation Optimizing Media Feeding Strategies Guidance for Cellvento (TM) CHO Media Platform", Jan. 1, 2016 (Jan. 1, 2016), XP05571 2557.

Schmidt C. et al., "Keto leucine and keto isoleucine are bioavailable precursors of their respective amino acids in cell culture media" J. of Biotechnology, Elsevier, 2020, vol. 321, pp. 1-12.

Schmidt C. et al., A big cheese in biotherapeutics: Lactoyl leucine and isoleucine are bioavailable 1 alternatives for canonical amino acids in cell culture media; downloaded from URL:https://www.authorea.com/users/395074/articles/508403/master/file/data/2021%2002%2006%20Lactoyl-AA%20paper_final%20for%20submission.pdf, 2021, pp. 1-22.

International Search Report PCT/EP2020/081695 dated Mar. 12, 2021 (pp. 1-5).

* cited by examiner tyrosine valine leucine isoleucine methionine phenylalanine tryptophane

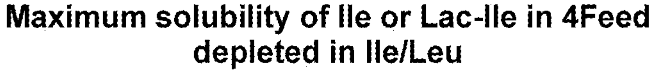
Fig. 2
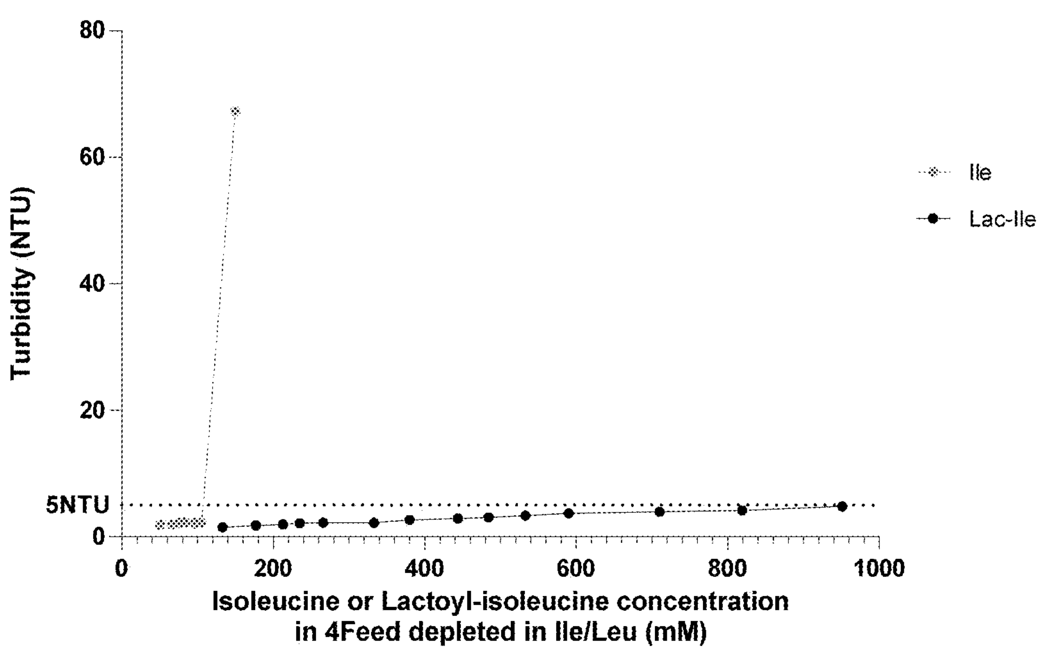

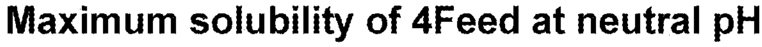
Fig. 4
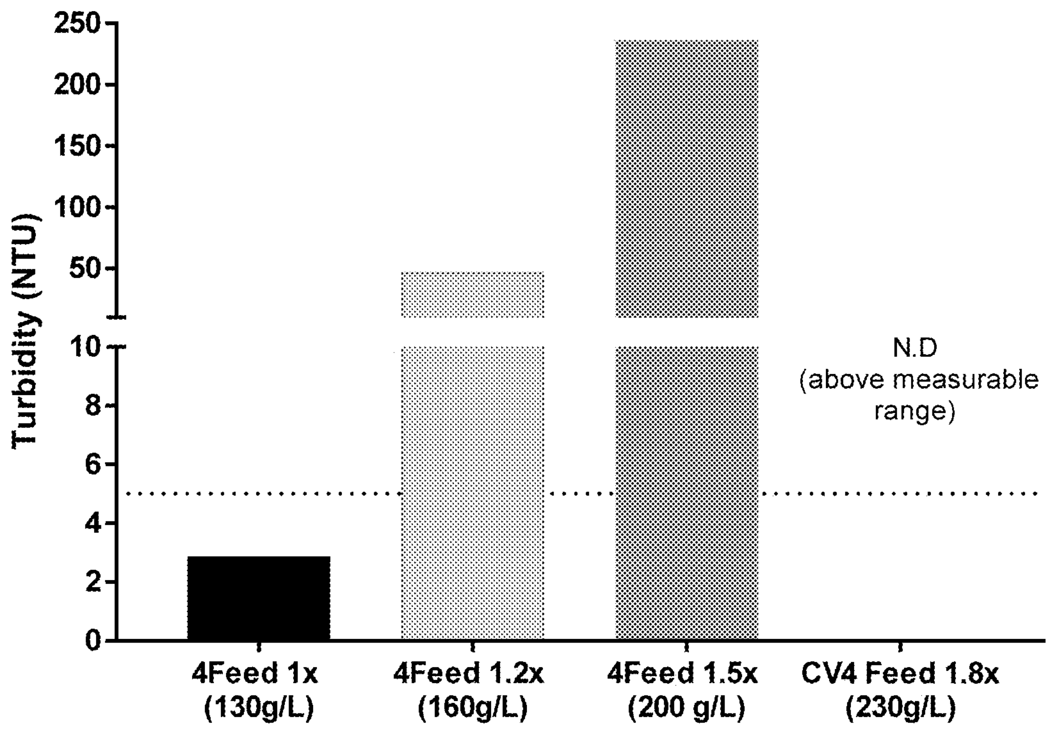
Maximum solubility of 4Feed at neutral pH
Turbidity (NTU)
250
200
150
100
50
10
8
6
4
2
0
N.D
(above measurable
range)
4Feed 1x
(130g/L)
4Feed 1.2x
(160g/L)
4Feed 1.5x
(200 g/L)
CV4 Feed 1.8x
(230g/L)

CELL CULTURE MEDIA

The present invention relates to cell culture media comprising N-lactoyl derivatives of one or more amino acid. The poor solubility of some amino acids in cell culture media is overcome by substituting them partially or fully with an N-lactoyl derivative.

Cell culture media support and maintain the growth of cells in an artificial environment.

Depending on the type of organism whose growth shall be supported, the cell culture media comprise a complex mixture of components, sometimes more than one hundred different components.

The cell culture media required for the propagation of mammalian, insect or plant cells are typically much more complex than the media to support the growth of bacteria and yeasts.

The first cell culture media that were developed consisted of undefined components, such as plasma, serum, embryo extracts, or other non-defined biological extracts or peptones. A major advance was thus made with the development of chemically defined media. Chemically defined media often comprise but are not exclusively limited to amino acids, vitamins, metal salts, antioxidants, chelators, growth factors, buffers, hormones, and many more substances known to those expert in the art.

Some cell culture media are offered as sterile aqueous liquids. The disadvantage of liquid cell culture media is their reduced shelf life and difficulties for shipping and storage. As a consequence, many cell culture media are presently offered as finely milled dry powder mixtures. They are manufactured for the purpose of dissolving in water and/or aqueous solutions and in the dissolved state are designed, often with other supplements, for supplying cells with a substantial nutrient base for growth and/or production of biopharmaceuticals from said cells.

Most biopharmaceutical production platforms are based on fed-batch cell culture protocols. The aim typically is to develop high-titer cell culture processes to meet increasing market demands and reduce manufacturing costs. Beside the use of high-performing recombinant cell lines, improvements in cell culture media and process parameters are required to realize the maximum production potentials.

In a fed-batch process, a basal medium supports initial growth and production, and a feed medium prevents depletion of nutrients and sustains the production phase. The media are chosen to accommodate the distinct metabolic requirements during different production phases. Process parameter settings—including feeding strategy and control parameters—define the chemical and physical environments suitable for cell growth and protein production.

Optimization of the feed medium is a major aspect in the optimization of a fed-batch process.

Mostly the feed medium is highly concentrated to avoid dilution of the product (antibody or recombinant proteins) in the bioreactor. The controlled addition of the nutrient directly affects the growth rate and the longevity of the culture.

Amino acids (AA) are essential components of cell culture media since they are key to support cellular growth. In addition, AA are key building blocks for recombinant proteins produced using mammalian cell culture technologies. The solubility of AA is a limiting factor hindering the concentration of cell culture media (CCM) and feed formulations. Such a concentration would be essential to develop next generation manufacturing platforms. Particularly, highly concentrated formulations are required for biomanufacturing processes using inline dilution, to reduce the volume of CCM which must be stored in tanks (=reduce manufacturing footprint) or in general to reduce the volume of feed added throughout a fed-batch (FB) process and thus potentially increase the volumetric titer.

Consequently it would be favourable to find a way to improve the solubility of amino acids.

Though N-lactoyl amino acids are known to be highly resistant to proteolysis (Lorbert S J et al: Oligomers and oligomeric segments of alpha-hydroxy carboxylic acids and alpha amino acids. US 2004/0048347, 2004), it has been unexpectedly found that amino acids can be replaced in cell culture media by their N-lactoyl derivatives or salts thereof. In addition to their use as amino acid sources, the N-lactoyl derivatives present a higher solubility compared to their corresponding amino acids and can therefore be used in highly concentrated formulations.

N-lactoyl amino acids are known in the food industry as taste active amino acids formed from free amino acids through the action of lactoyl transferase in *lactobacillus* spp., particularly in food like soy sauce and meat products (Zhao C J, Schieber A, Ganzle M G: Formation of taste-active amino acids, amino acid derivatives and peptides in food fermentations—A review. *Food Res Int* 2016, 89(Pt 1):39-47.).

N-lactoyl-amino acids have also been described in the context of medicine or human cellular models. According to a study of Jansen R S et al, N-lactoyl-amino acids are ubiquitous metabolites that originate from CNDP2-mediated reverse proteolysis of lactate and amino acids (*Proc Natl Acad Sci USA* 2015, 112(21):6601-6606). In a very recent study, N-lactoyl-amino acids are described as extracellular biomarkers that correlate with the intracellular amino acid concentration in human cellular models. The derivatives are described as useful biomarkers to differentiate between tumor and normal cells: Knott M E, Manzi M, Zabalegui N, Salazar M O, Puricelli L I, Monge M E: Metabolic Footprinting of a Clear Cell Renal Cell Carcinoma in Vitro Model for Human Kidney Cancer Detection. J Proteome Res 2018, 17(11):3877-3888.

N-lactoyl-amino acids as cell culture media ingredients are not known.

The present invention is therefore directed to cell culture media comprising at least one N-lactoyl-amino acid. If in the following the term amino acid is used, it means the free amino acid as well as salts thereof like the $Na^+$, $K^+$, $Mg^{2+}$, $Ca^{2+}$, $Li^+$, preferably $Na^+$ salt thereof. A person skilled in the art is aware that either the free amino acid can be used or the $H^+$ can be substituted by a metal counterion like $Na^+$ so that the salt is generated.

In a preferred embodiment, the N-lactoyl-amino acid is selected from N-lactoyl-leucine, N-lactoyl-isoleucine, N-lactoyl-valine, N-lactoyl-phenylalanine, N-lactoyl-tyrosine and/or N-lactoyl-methionine, most preferably N-lactoyl-leucine and/or N-lactoyl-isoleucine.

In a preferred embodiment the cell culture medium comprises one or more of the components of formula I:

I

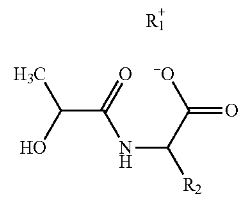

with $R_1^+$ being $H^+$ or a metal ion like $Na^+$, $K^+$, $Mg^{2+}$, $Ca^{2+}$, $Li^+$, preferably $Na^+$, $R_2$ being the characteristic residue of the amino acid. In case of the amino acid being leucine, the component of formula I would be

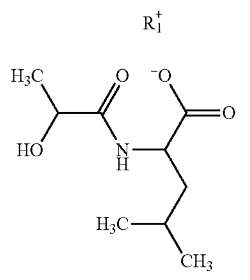

In case of the amino acid being isoleucine, the component of formula I would be

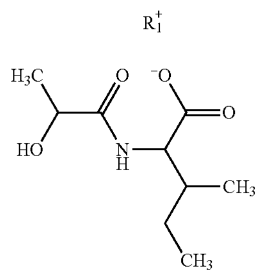

In a preferred embodiment, the cell culture medium comprises the sodium salt of the N-lactoyl amino acid. That means, preferably $R_1^+$ is $Na^+$.

In a preferred embodiment, the cell culture medium is a dry powder medium.

In one embodiment, especially if the cell culture medium is a basal medium or a perfusion cell culture medium, it comprises one or more N-lactoyl amino acids as well as the corresponding native amino acids. That means it comprises for example N-lactoyl-leucine and the corresponding native leucine. Native in this case means the unmodified amino acid and/or a salt thereof.

In another preferred embodiment, the cell culture medium is a feed medium.

The feed medium may comprise one or more N-lactoyl amino acids and the corresponding native amino acids but it may also only comprise one or more N-lactoyl amino acids and not the corresponding native amino acids. In a preferred embodiment, if the cell culture medium is a feed medium, the medium comprises one or more N-lactoyl amino acids but not the corresponding native amino acids.

In another preferred embodiment the cell culture medium is a liquid medium having a pH of 8.5 or less and comprising at least one N-lactoyl amino acid according to formula I in a concentration above 10 mmol/l. In case of feed media the concentration is typically above 30 mmol/l. The upper limit is only defined by the solubility of the lactoyl amino acids. The solubility may depend on the solvent, the pH and the salt concentration. Consequently, it is typically possible to generate liquid media with a concentration of the lactoyl amino acid of up to 500 mmol/l or more.

In a preferred embodiment the pH of the liquid medium is between 6.0 and 8.5, most preferred between 6.5 and 7.8.

In one embodiment, the cell culture medium comprises at least one or more saccharide components, one or more amino acids, one or more vitamins or vitamin precursors, one or more salts, one or more buffer components, one or more co-factors and one or more nucleic acid components.

The present invention is further directed to a method for producing a cell culture medium according to the present invention by a) mixing one or more N-lactoyl-amino acid according to formula I with the other components of the cell culture medium b) subjecting the mixture of step a) to milling In a preferred embodiment step b) is performed in a pin mill, fitz mill or a jet mill.

In another preferred embodiment, the mixture from step a) is cooled to a temperature below 0° C. prior to milling.

The present invention is further directed to a process for culturing cells by a) providing a bioreactor b) mixing the cells to be cultured with a cell culture medium according to the present invention.

c) incubating the mixture of step b).

In one embodiment, the bioreactor is a perfusion bioreactor.

The present invention is also directed to a fed batch process for culturing cells in a bioreactor by Filling into a bioreactor cells and an aqueous cell culture medium Incubating the cells in the bioreactor Adding a cell culture medium, which is in this case a feed medium, to the bioreactor, continuously over the whole time or once or several times within the cells incubation time whereby the feed medium is a cell culture medium according to the present invention comprising at least one N-lactoyl amino acid.

Preferably the feed medium has a pH below pH 8.5 and comprises at least one N-lactoyl amino acid in a concentration above 10 mmol/l.

Preferably, the N-lactoyl amino acids are N-lactoyl leucine and/or N-lactoyl isoleucine.

FIG. 1 shows exemplary structures of native amino acids with their characteristic residues.

Further details about FIGS. 2 to 20 can be found in the Examples.

A N-lactoyl amino acid is an amino acid which is covalently linked via its amino group to a lactoyl residue. A lactoyl residue is the chemical moiety $CH_3CH(OH)CO—$ of lactic acid.

A N-lactoyl amino acid according to the present invention is a product e.g. obtainable by chemical or biological synthesis.

N-lactoyl amino acids can be synthesized in vivo and in microorganisms through enzymes like the lactoyl transferase in *lactobacillus* spp. (Zhao C J, Schieber A, Ganzle M G: Formation of taste-active amino acids, amino acid derivatives and peptides in food fermentations—A review. *Food Res Int* 2016, 89(Pt 1):39-47) or by CNDP2-mediated reverse proteolysis (Jansen R S, et al: N-lactoyl-amino acids are ubiquitous metabolites that originate from CNDP2-mediated reverse proteolysis of lactate and amino acids. *Proc Natl Acad Sci USA* 2015, 112(21):6601-6606).

Synthesis of N-lactoyl amino acids using a biocatalysis approach was also described in a mixture containing an enzyme (e.g. enzyme catalysing the formation of peptide bonds such as serine proteinases, thiol proteinases, metalloproteinases, esterase or alkaline protease), an alpha-hydroxycarboxylic acid (or derivative such as corresponding ester, acid halide, amide, anhydride or ketene) and an alpha amino acid (or derivative such as corresponding ester, acid halide, amide, anhydride or ketene) (Lorbert S J et al: Oligomers and oligomeric segments of alpha-hydroxy carboxylic acids and alpha amino acids. US 2004/0048347, 2004).

Several chemical processes have been described for the synthesis of N-lactoyl amino acids. The synthesis of Lac-Phe from Sforza S, Cavatorta V, Galaverna G, Dossena A, Marchelli R: Accumulation of non-proteolytic aminoacyl derivatives in Parmigiano-Reggiano cheese during ripening. *International Dairy Journal* 2009, 19(10):582-587, is exemplarily described in Example 1.

Other synthesis processes have been described in the literature, for example Lac-Glu has been synthesized in Frerot E, Chen T: Identification and quantitation of new glutamic acid derivatives in soy sauce by UPLC/MS/MS. Chem Biodivers 2013, 10(10):1842-1850, from L-lactic acid and L-glutamic acid ester to yield mainly the L form of the Lac-AA. Characterization was performed using LC-MS SRM. Similarly, Lac-Val was synthesized in two steps from L-lactic acid and H-Val-OBzI tosylate salt with an overall yield of 56% after hydrogenolysis. Finally, the synthesis through a single coupling reaction between the amino ester-protected amino acids and (+)-(S)-lactic acid in the presence of one equivalent of PyBOP® (benzotriazolyloxy-tris[pyrrolidino]-phosphonium hexafluorophosphate) and excess diisopropyl ethylamine was described in Frerot E, Escher D: Flavored products and a process for their preparation. U.S. Pat. No. 5,780,090, 1998. NMR and LC-MS data were provided for Lac-Glu, Lac-Ala, Lac-Leu, Lac-Ile, N-lactoyl-Tyrosine (Lac-Tyr) and Lac-Met.

N-lactoyl amino acids are preferably compounds according to formula I.

I

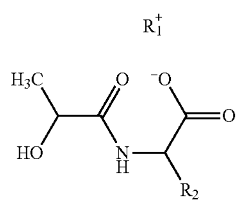

with $R_1^+$ being $H^+$ or a metal ion like $Na^+$, $K^+$, $Mg^{2+}$, $Ca^{2+}$, $Li^+$, preferably $Na^+$, $R_2$ being the characteristic residue of the amino acid.

The characteristic residue of the amino acids is the unique portion of an amino acid. The characteristic residue is the part that gives the amino acid its characteristic properties so that it can be distinguished from other amino acids. For example, some characteristic amino acid residues are polar, other are non-polar, some characteristic amino acid residues are aliphatic, others are aromatic. FIG. 1 shows the general structure of amino acids with some exemplary characteristic residues $R_2$.

A cell culture medium according to the present invention is any mixture of components which maintains and/or supports the in vitro growth of cells. It might be a complex medium or a chemically defined medium. The cell culture medium can comprise all components necessary to maintain and/or support the in vitro growth of cells or only some components so that further components are added separately. Examples of cell culture media according to the present invention are full media which comprise all components necessary to maintain and/or support the in vitro growth of cells as well as media supplements or feeds. In a preferred embodiment, the cell culture medium is a full medium or a feed medium. A full medium also called basal medium typically has a pH between 6.5 and 7.8. A feed medium preferably has a pH below 8.5, preferably between 6.0 and 8.5.

Typically, the cell culture media according to the invention are used to maintain and/or support the growth of cells in a bioreactor.

A feed or feed medium is a cell culture medium which is not the basal medium that supports initial growth and production in a cell culture but the medium which is added at a later stage to prevent depletion of nutrients and sustains the production phase. A feed medium can have higher concentrations of some components compared to a basal culture medium. For example, some components, such as, for example, nutrients including amino acids or carbohydrates, may be present in the feed medium at about 5×, 6×, 7×, 8×, 9×, 10×, 12×, 14×, 16×, 20×, 30×, 50×, 100×, 200×, 400×, 600×, 800×, or even about 1000× of the concentrations in a basal medium.

A mammalian cell culture medium is a mixture of components which maintain and/or support the in vitro growth of mammalian cells. Examples of mammalian cells are human or animal cells, preferably CHO cells, COS cells, I VERO cells, BHK cells, AK-1 cells, SP2/0 cells, L5.1 cells, hybridoma cells or human cells.

Chemically defined cell culture media are cell culture media that do not comprise any chemically undefined substances. This means that the chemical composition of all the chemicals used in the media is known. The chemically defined media do not comprise any yeast, animal or plant tissues; they do not comprise feeder cells, serum, extracts or digests or other components which may contribute to chemically poorly defined proteins in the media. Chemically undefined or poorly defined chemical components are those whose chemical composition and structure is not known, are present in varying composition or could only be defined with enormous experimental effort—comparable to the evaluation of the chemical composition and structure of a protein like albumin or casein.

A powdered cell culture medium or a dry powder medium is a cell culture medium typically resulting from a milling process, a lyophilisation process or a dry or wet granulation process. That means the powdered cell culture medium is a granular, particulate medium—not a liquid medium. The term "dry powder" may be used interchangeably with the term "powder;" however, "dry powder" as used herein simply refers to the gross appearance of the granulated material and is not intended to mean that the material is completely free of complexed or agglomerated solvent unless otherwise indicated. Dry powder media resulting from a milling or lyophilisation process typically have particle sizes below 0.5 mm, e.g. between 0.05 and 0.5 mm.

Dry powder media resulting from dry or wet granulation process, e.g. by spray drying, wet granulation or dry compaction, typically have particle sizes above 0.5 mm, e.g. between 0.5 and 5 mm. Dry compaction is typically done in a roll press. U.S. Pat. No. 6,383,810 B2 discloses a method of producing an agglomerated eukaryotic cell culture medium powder. The method comprises wetting a dry powder cell culture medium with a solvent and then re-drying the moistened medium to obtain a dry agglomerated cell culture medium.

In one embodiment the dry powder media according to the present invention are produced by dry compaction.

Cells to be cultured with the media according to the present invention may be prokaryotic cells like bacterial cells or eukaryotic cells like plant or animal cells. The cells can be normal cells, immortalized cells, diseased cells, transformed cells, mutant cells, somatic cells, germ cells, stem cells, precursor cells or embryonic cells, any of which may be established or transformed cell lines or obtained from natural sources.

The size of a particle means the mean diameter of the particle. If the size of particles is given it means that at least 80%, preferably at least 90%, of the particles have the given particle size or are in the given particle size range. The particle diameter is determined by laser light scattering.

An inert atmosphere is generated by filling the respective container or apparatus with an inert gas. Suitable inert gases are noble gases like argon or preferably nitrogen. These inert gases are non-reactive and prevent undesirable chemical reactions from taking place. In the process according to the present invention, generating an inert atmosphere means that the concentration of oxygen is reduced below 10% (v/v) absolute, e.g. by introducing liquid nitrogen or nitrogen gas.

Different types of mills are known to a person skilled in the art.

A pin mill, also called centrifugal impact mill, pulverizes solids whereby protruding pins on high-speed rotating disks provide the breaking energy. Pin mills are for example sold by Munson Machinery (USA), Premium Pulman (India) or Sturtevant (USA).

A jet mill uses compressed gas to accelerate the particles, causing them to impact against each other in the process chamber. Jet mills are e.g. sold by Sturtevant (USA) or PMT (Austria).

A fitz mill commercialized by Fitzpatrick (USA), uses a rotor with blades for milling.

A process that is run continuously is a process that is not run batchwise. If a milling process is run continuously it means that the media ingredients are permanently and steadily fed into the mill over a certain time.

The cell culture media, especially the full media, according to the present invention typically comprise at least one or more saccharide components, one or more amino acids, one or more vitamins or vitamin precursors, one or more salts, one or more buffer components, one or more co-factors and one or more nucleic acid components.

The media may also comprise sodium pyruvate, insulin, vegetable proteins, fatty acids and/or fatty acid derivatives and/or pluronic acid and/or surface active components like chemically prepared non-ionic surfactants. One example of a suitable non-ionic surfactant are difunctional block copolymer surfactants terminating in primary hydroxyl groups also called poloxamers, e.g. available under the trade name pluronic® from BASF, Germany.

Saccharide components are all mono- or di-saccharides, like glucose, galactose, ribose or fructose (examples of monosaccharides) or sucrose, lactose or maltose (examples of disaccharides).

Examples of amino acids according to the invention are tyrosine, the proteinogenic amino acids, especially the essential amino acids, leucine, isoleucine, lysine, methionine, phenylalanine, threonine, tryptophan and valine, as well as the non-proteinogenic amino acids, preferably the L-amino acids.

Tyrosine means L- or D-tyrosine, preferably L-tyrosine.

Cysteine means L- or D-cysteine, preferably L-cysteine.

Examples of vitamins are Vitamin A (Retinol, retinal, various retinoids, and four carotenoids), Vitamin $B_1$ (Thiamine), Vitamin $B_2$ (Riboflavin), Vitamin $B_3$ (Niacin, niacinamide), Vitamin $B_5$ (Pantothenic acid), Vitamin $B_6$ (Pyridoxine, pyridoxamine, pyridoxal), Vitamin $B_7$ (Biotin), Vitamin $B_9$ (Folic acid, folinic acid), Vitamin $B_{12}$ (Cyanocobalamin, hydroxycobalamin, methylcobalamin), Vitamin C (Ascorbic acid), Vitamin D (Ergocalciferol, cholecalciferol), Vitamin E (Tocopherols, tocotrienols) and Vitamin K (phylloquinone, menaquinones). Vitamin precursors are also included.

Examples of salts are components comprising inorganic ions such as bicarbonate, calcium, chloride, magnesium, phosphate, potassium and sodium or trace elements such as Co, Cu, F, Fe, Mn, Mo, Ni, Se, Si, Ni, Bi, V and Zn. Examples are Copper(II) sulphate pentahydrate ($CuSO_4.5H_2O$), Sodium Chloride (NaCl), Calcium chloride ($CaCl_2.2H_2O$), Potassium chloride (KCl), Iron(II)sulphate, sodium phosphate monobasic anhydrous ($NaH_2PO_4$), Magnesium sulphate anhydrous ($MgSO_4$), sodium phosphate dibasic anhydrous ($Na_2HPO_4$), Magnesium chloride hexahydrate ($MgCl_2.6H_2O$), zinc sulphate heptahydrate.

Examples of buffers are $CO_2/HCO_3$ (carbonate), phosphate, HEPES, PIPES, ACES, BES, TES, MOPS and TRIS.

Examples of cofactors are thiamine derivatives, biotin, vitamin C, NAD/NADP, cobalamin, flavin mononucleotide and derivatives, glutathione, nucleotides, phosphates and derivatives.

Nucleic acid components, according to the present invention, are the nucleobases, like cytosine, guanine, adenine, thymine or uracil, the nucleosides like cytidine, uridine, adenosine, guanosine and thymidine, and the nucleotides like adenosine monophosphate or adenosine diphosphate or adenosine triphosphate.

Feed media may have a different composition compared to full media. They typically comprise amino acids, trace elements and vitamins. They might also comprise saccharide components but sometimes for production reasons the saccharide components are added in a separate feed.

A suitable feed medium might for example comprise one or more of the following compounds:

L-ASPARAGINE MONOHYDRATE
L-ISOLEUCINE
L-PHENYLALANINE
SODIUM L-GLUTAMATE MONOHYDRATE
L-LEUCINE
L-THREONINE
L-LYSINE MONOHYDROCHLORIDE
L-PROLINE
L-SERINE
L-ARGININE MONOHYDROCHLORIDE
L-HISTIDINE MONOHYDROCHLORIDE MONOHYDRATE
L-METHIONINE
L-VALINE
MONO-SODIUM-L-ASPARTATE-MONOHYDRATE
L-TRYPTOPHAN
CHOLINE CHLORIDE
MYO-INOSITOL
NICOTINAMIDE
CALCIUM-D(+) PANTOTHENATE
PYRIDOXINE HYDROCHLORIDE
THIAMINE CHLORIDE HYDROCHLORIDE
VITAMIN B12 (CYANOCOBALAMINE) MICRONIZED

BIOTIN
FOLIC ACID
RIBOFLAVIN
MAGNESIUM SULFATE ANHYDROUS
COPPER(II) SULFATE PENTAHYDRATE
ZINC SULFATE HEPTAHYDRATE
1,4-DIAMINOBUTANE DIHYDRCHLORIDE
AMMONIUM HEPTAMOLYBDATE TETRAHYDRATE
CADMIUM SULFATE HYDRATE
MANGANESE(II) CHLORIDE TETRAHYDRATE
NICKEL(II) CHLORIDE HEXAHYDRATE
SODIUM META SILICATE
SODIUM METAVANADATE
TIN(II) CHLORIDE DIHYDRATE
SODIUM SELENITE (ABOUT 45% SE)
SODIUM DIHYDROGEN PHOSPHATE MONOHYDRATE
AMMONIUM IRON(III) CITRATE (ABOUT 18% FE)

Freezing according to the present invention means cooling to a temperature below 0° C.

The gist of the present invention is to provide powdered cell culture media, like e.g. dry powder media made by dry compaction, that can be easily dissolved in a suitable solvent by just admixing the powder and the solvent such that the powder dissolves and produces a liquid cell culture medium suitable for culturing cells such as a full medium, a medium supplement, a medium subgroup or a feed with a desired and homogenous concentration of the media components.

The simple dissolving of a powdered cell culture medium is often complicated by substances, especially amino acids, which have a poor solubility in aqueous solvents. L-tyrosine for example has a solubility of 0.4 g/l in water at a temperature of 25° C. That means about 0.4 g of L-tyrosine are soluble in 1 liter of water. But the required concentration of tyrosine in cell culture media is often higher. Also the solubility of leucine with about 22.1 g/kg at 25° C. and of isoleucine with 32.4 g/kg at 25° C. are often regarded as being insufficient.

It has been found that the N-lactoyl derivatives of amino acids, on the one hand, typically have a higher solubility in aqueous solutions and on the other hand, can be used as substitutes for the respective amino acids and are equally suitable as cell culture media component as the corresponding native amino acids.

Preferably, to achieve optimal performance, the cell culture media according to the present invention comprise the native amino acids as well as the N-lactoyl amino acid. In case the media is a feed media, or another media additive, that is added to a basal medium comprising the native amino acids, the said feed media or media additive might only comprise the N-lactoyl amino acid but not the corresponding native amino acids.

Typically in base media and perfusion media the molar ratio between the N-lactoyl amino acid and the corresponding native amino acid is between 5:1 and 1:5, preferably between 5:1 and 1:1

The overall concentration of each lactoyl amino acid in a ready to use liquid basic/perfusion medium and also in a feed medium or medium additive is very flexible. The upper limit is only defined by the solubility of the lactoyl amino acids in the respective medium. Consequently, it is typically possible to generate liquid media with a concentration of the lactoyl amino acid of up to 500 mmol/l or more.

The solubility of the N-lactoyl amino acids is higher than that of the respective native amino acid (see table 1 and table 2 in Example 2). To enlarge the solubility of the N-lactoyl amino acids even more, a salt can be formed by reacting the derivative with a suitable base. The sodium salts are preferred.

A cell culture medium according to the present invention can comprise one or more, that means for example one, two, three, four, five, six, seven, eight, nine or ten of the N-lactoyl amino acids.

The powdered cell culture media of the present invention are preferably produced by mixing all components and milling them. The mixing of the components is known to a person skilled in the art of producing dry powdered cell culture media by milling. Preferably, all components are thoroughly mixed so that all parts of the mixture have nearly the same composition. The higher the uniformity of the composition, the better the quality of the resulting medium with respect to homogenous cell growth. The milling can be performed with any type of mill suitable for producing powdered cell culture media. Typical examples are ball mills, pin mills, fitz mills or jet mills. Preferred is a pin mill, a fitz mill or a jet mill, very preferred is a pin mill.

A person skilled in the art knows how to run such mills.

A large scale equipment mill with a disc diameter of about 40 cm is e.g. typically run at 1-6500 revolutions per minute in case of a pin mill, preferred are 1-3000 revolutions per minute.

The milling can be done under standard milling conditions resulting in powders with particle sizes between 10 and 300 μm, most preferably between 25 and 120 μm.

Preferably, all components of the mixture which is subjected to milling are dry. This means, if they comprise water, they do only comprise water of crystallization but not more than 10%, preferably not more than 5% most preferred not more than 2% by weight of unbound or uncoordinated water molecules.

In a preferred embodiment, the milling is performed in an inert atmosphere. Preferred inert protective gas is nitrogen.

In another preferred embodiment, all components of the mixture are freezed prior to milling. The freezing of the ingredients prior to the milling can be done by any means that ensures a cooling of the ingredients to a temperature below 0° C. and most preferably below −20° C. In a preferred embodiment the freezing is done with liquid nitrogen. This means the ingredients are treated with liquid nitrogen, for example by pouring liquid nitrogen into the container in which the ingredients are stored prior to introduction into the mill. In a preferred embodiment, the container is a feeder. If the container is a feeder the liquid nitrogen is preferably introduced at the side or close to the side of the feeder at which the ingredients are introduced.

Typically the ingredients are treated with the liquid nitrogen over 2 to 20 seconds.

Preferably the cooling of the ingredients is done in a way that all ingredients that enter into the mill are at a temperature below 0° C., most preferred below −20° C.

In a preferred embodiment, all ingredients are put in a container from which the mixture is transferred in a feeder, most preferred in a metering screw feeder. In the feeder the ingredients are sometimes further mixed—depending on the type of feeder—and additionally cooled. The cooled mixture is then transferred from the feeder to the mill so that the mixture which is milled in the mill preferably still has a temperature below 0° C., more preferred below −20° C.

Typically the blending time, that means the residence time of the mixture of ingredients in the feeder is more than one minute, preferably between 15 and 60 minutes.

A metering screw feeder, also called dosage snail, is typically run at a speed of 10 to 200 revolutions per minute, preferably it is run at 40 to 60 revolutions per minute.

Typically, the temperature of the mill is kept between −50 and +30° C. In a preferred embodiment, the temperature is kept around 10° C.

The oxygen level during milling preferably is below 10% (v/v).

The process can be run e.g. batch-wise or continuously. In a preferred embodiment the process according to the present invention is done continuously by, over a certain time, permanently filling the mixture of ingredients into a feeder for cooling and permanently filling cooled mixture from the feeder into the mill.

After milling, the resulting dry powder medium might be further compacted to enlarge the size of the particles, e.g. by dry compaction in a roll press.

For use of the powdered media a solvent, preferably water (most particularly distilled and/or deionized water or purified water or water for injection) or an aqueous buffer is added to the media and the components are mixed until the medium is totally dissolved in the solvent and the ready to use liquid medium is generated.

The solvent may also comprise saline, soluble acid or base ions providing a suitable pH range (typically in the range between pH 1.0 and pH 10.0), stabilizers, surfactants, preservatives, and alcohols or other polar organic solvents.

It is also possible to add further substances like buffer substances for adjustment of the pH, fetal calf serum, sugars etc. to the mixture of the cell culture medium and the solvent. The resulting liquid cell culture medium is then contacted with the cells to be grown or maintained.

While media compositions comprising a higher concentration of one or more native amino acid would show turbidity when mixed with the solvent due to the non-dissolved amino acids, the cell culture media according to the present invention in which the amino acids are fully or partly substituted by the corresponding N-lactoyl amino acid give clear solutions, as shown by the turbidity measurement in Example 3 and FIGS. 2 and 3.

The present invention is further directed to a process for culturing cells by a) providing a bioreactor b) mixing the cells to be cultured with a cell culture medium according to the present invention c) incubating the mixture of step b)

In one embodiment the bioreactor is a perfusion bioreactor.

A bioreactor is any vessel or tank in which cells can be cultured. Incubation is typically done under suitable conditions like suitable temperature etc. A person skilled in the art is aware of suitable incubation conditions for supporting or maintaining the growth/culturing of cells.

A perfusion bioreactor is a bioreactor in which perfusion cell culture can be performed. It comprises the bioreactor vessel which is typically closed during cell culture, a stirrer in the vessel, a line for introducing fresh medium, a harvest line for removing the harvest stream comprising cells, liquid medium and target product from the bioreactor and a cell retention device in the harvest line that retains the cells while the liquid part of the harvest can be collected. A review about perfusion cell culture providing details about favorable set ups can be found in "Perfusion mammalian cell culture for recombinant protein manufacturing—A critical review" Jean-Marc Bielser et al., Biotechnology Advances 36 (2018) 1328-1340

It has been found that the present invention is also very suitable for the preparation of feed media. Due to the limitations in the availability of certain amino acids especially in the concentrations necessary for feed media the feed media cannot be prepared in the desired high concentrations or they need to be prepared under drastic pH condition like very basic pH. This might negatively affect the nutrition supply to cells and to some extent accelerate cell death by exposure to extreme basic pH values.

Consequently here is a need for feed media that comprise all needed components in one feed and at high concentrations. In addition the pH of the feed should not negatively influence the cell culture.

It has been found that N-lactoyl amino acids have an improved solubility and can be used in highly concentrated feed media instead of the corresponding native amino acid without any negative effect and sometimes even positive effect on the cell growth and/or productivity at a pH below 8.5.

The present invention is thus also directed to a feed medium either in form of a powdered medium or after dissolution in form of a liquid medium.

The resulting liquid medium comprises one or more N-lactoyl amino acid in concentrations typically above 10 mmol/l or even above 50 mmol/l and preferably has a pH of 8.5 or less.

In a preferred embodiment, the pH is between 6.5 and 7.8.

The present invention is also directed to a process for culturing cells in a bioreactor by Filling into a bioreactor cells and an aqueous cell culture medium Incubating the cells in the bioreactor Adding a cell culture medium to the bioreactor, continuously over the whole time or once or several times within the cells incubation time whereby the cell culture medium that is added preferably has a pH of less than pH 8.5 and comprises at least one N-lactoyl amino acid. Typically the medium comprises between 50 and 150 g/l of solid ingredients that are dissolved in the solvent.

In one embodiment the medium that is added is a feed medium and the process is a fed batch process. In another medium the medium that is added is a perfusion medium and the process is a perfusion process.

It has been found that by using one or more N-lactoyl amino acids a feed medium can be obtained that comprises all necessary feed components at high concentrations (overall concentration between 100 and 250 g/1). In contrast to known processes where two or more different feed media need to be fed to the bioreactor, the present invention provides a medium and a method which enables the use of one feed medium that comprises all components in high concentrations. In addition the pH of the feed medium according to the present invention typically is below 8.5.

In a preferred embodiment, in the process of the present invention the feed medium that is added during the incubation either continuously or once or several times within said time to the bioreactor always has the same composition.

The present invention is further illustrated by the following figures and examples, however, without being restricted thereto.

The entire disclosure of all applications, patents, and publications cited above and below as well as the corresponding European patent application EP 19209150.2, filed on Nov. 14, 2019, are hereby incorporated by reference.

EXAMPLES

The following examples represent practical applications of the invention.

Example 1 Synthesis of L-lactoyl-L-phenylalanine

L-lactoyl-L-phenylalanine was synthesized starting from free phenylalanine (Sforza, S., et al., Accumulation of non-proteolytic aminoacyl derivatives in Parmigiano-Reggiano cheese during ripening. International Dairy Journal, 2009. 19(10): p. 582-587). L-phenylalanine methyl ester hydrochloride was first synthesized: 2.00 g of L-phenylalanine (12.05 mmol) were dissolved in 100 mL of methanol and kept under continuous stirring in an ice bath; $SOCl_2$ was slowly added up to a final concentration of 1 M. The reaction was monitored by TLC (eluent: n-butanol:acetic acid:$H_2O$, 4:1:1, by vol; UV and ninhydrin detection, Rf of 0.6) and took place overnight. The reaction mixture was dried under vacuum, methanol was added and evaporated again under reduced pressure (4 times) to eliminate completely the HCl; crude yield was 98%. (S)-2-acetoxypropionic acid (0.41 g, 3.12 mmol) was then dissolved in 4 mL of $CH_2Cl_2$ together with 1.12 g (2.96 mmol) of HBTU and the mixture was kept under continuous stirring at room temperature for 30 min, in order to activate the carboxylic function. The L-Phenylalanine-methyl ester hydrochloride previously synthesized (0.68 g, 3.12 mmol) was dissolved in 4 mL of $CH_2Cl_2$, together with DIPEA (1.54 mL, 9.36 mmol) and then added to the activated acetoxypropionic acid. The reaction was left under magnetic stirring for 4 h at room temperature. The reaction was monitored by TLC (eluent: ethyl acetate; UV absorbance detector, Rf of 0.8). The organic solution was then washed with saturated solutions of $KHSO_4$ (three times) and $NaHCO_3$(three times), dried over $MgSO_4$ and filtered and the product was dried under vacuum; crude yield was 46%. The methyl and the acetyl protecting groups were then removed by reacting the product in a mixture of 0.34 g (1.296 mmol) of $Ba(OH)_2.5H_2O$ in 20 mL of tetrahydrofurane (THF)/$H_2O$ (1:1, v/v) for 20 min at 0° C. THF was then eliminated under vacuum, and the aqueous solution was acidified to pH 3.0 with HCl. The resulting solution was analysed by LC/ESI-MS.

Example 2: Lac-Ile and Lac-Leu have an Increased Solubility Compared to their Respective Amino Acids in Water The maximum solubility of Ile and Leu was compared with the solubility of their respective Lactoyl derivatives or salts thereof in water at 25° C. through the preparation of a saturated solution. After sedimentation, the solution was dried using infrared (120° C., 120 min) and the residual mass was determined in g/kg.

As shown in Table 1, the solubility of lactoyl-AA and salt thereof was significantly higher when compared to the solubility of the respective amino acid in water. For Leu, the increase in solubility was around 30-fold with Lac-Leu (N-lactoyl leucine) whereas the increase was 20-fold for Lac-Ile (N-lactoyl isoleucine) when compared to Ile. To exclude that the increase in solubility was due to the sodium salt form of the lactoyl-AA, separate experiments were performed to compare the solubility of Leu, Leu sodium salt and lac-Leu sodium salt. The maximum solubilities obtained in water were 22.1, 86.0 and 689.2 g/kg respectively indicating that, as expected, the formation of a sodium salt increases already the solubility of Leu but the increase in solubility obtained with the lactoyl derivative was significantly more important and thus cannot be due to only the salt form. The same behavior is considered valid for the other lac-AA. Altogether, these results indicate that lac-AA and their salts are suitable candidates to increase the solubility of cell culture media and feed formulations by replacement of their respective amino acid.

TABLE 1

Solubility of amino acids and their respective lac-AA or salts thereof in water at 25° C. Solubility experiments were performed using a saturated solution and residual mass determination after infrared drying.

| Amino acid | Chemical formula | Solubility 25° C. in g/kg | Corresponding Lac-AA | Availability | Chemical formula | Solubility 25° C. in g/kg |
|---|---|---|---|---|---|---|
| Leucine | 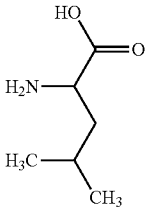 | 22.1 | Lac-Leu sodium salt | Own synthesis | 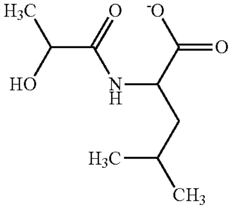 | 689.2 |
| Isoleucine | 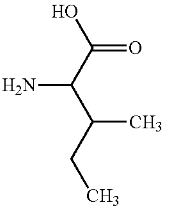 | 32.4 | Lac-Ile sodium salt | Own synthesis | 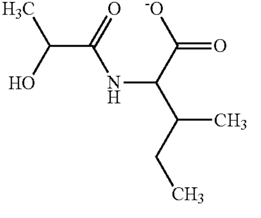 | 639.3 |

TABLE 1-continued

| Amino acid | Chemical formula | Solubility 25° C. in g/kg | Corresponding Lac-AA | Availability | Chemical formula | Solubility 25° C. in g/kg |
|---|---|---|---|---|---|---|
| Solubility of amino acids and their respective lac-AA or salts thereof in water at 25° C. Solubility experiments were performed using a saturated solution and residual mass determination after infrared drying. | | | | | | |
| Valine | 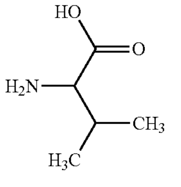 | 57.8 | Lac-Val sodium salt | Own synthesis | 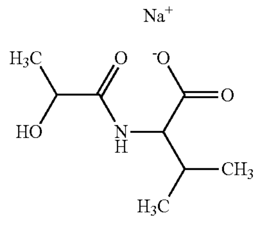 | 91.5 |
| Phenylalanine | 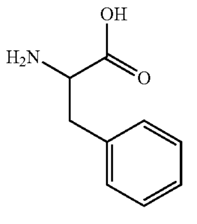 [SMILES: NC(Cc1ccccc1)C(=O)O] | 26.0 | Lac-Phe sodium salt | Own synthesis | 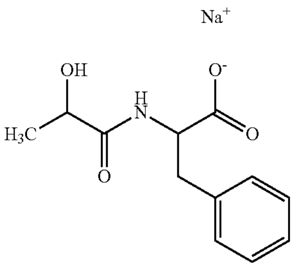 [SMILES: [Na+] ; CC(O)C(=O)NC(Cc1ccccc1)C(=O)[O-]] | 483.1 |
| Tyrosine | 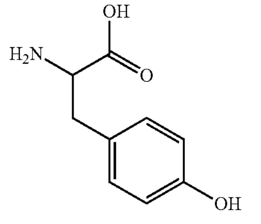 [SMILES: NC(Cc1ccc(O)cc1)C(=O)O] | 0.5 | Lac-Tyr sodium salt | Own synthesis | 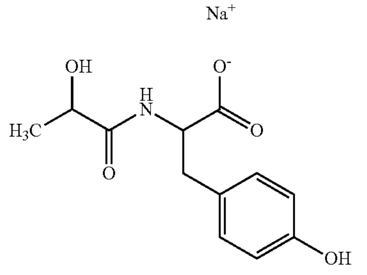 [SMILES: [Na+] ; CC(O)C(=O)NC(Cc1ccc(O)cc1)C(=O)[O-]] | 101.9 |
| Methionine | 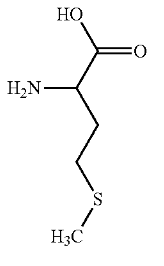 | 52.9 | Lac-Met sodium salt | Own synthesis | 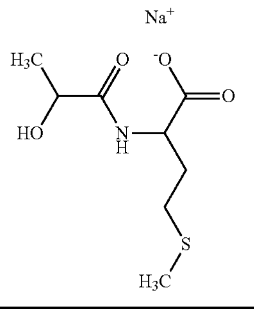 | 279.3 |

Example 3: Maximum Solubility of Lac-AA when Compared to their Respective Amino Acids in Cellvento® 4Feed Depleted in Ile and Leu Increasing amounts of the Lac-Leu and Lac-Ile and salts thereof were added to a cell culture feed formulation (Cellvento® 4Feed) depleted in Ile and Leu. Similarly, increasing amounts of Ile and Leu were added to the same feed formulation as a control. The total concentration of this feed formulation was 113 g/L and the pH was 7.0+/−0.2. In small scale experiments, after each addition of either the amino acid or the Lac-AA, the feed was agitated for 10 mins and turbidity was measured. The experiments were performed at room temperature (25° C.).

The maximum solubility of Ile in Cellvento® 4Feed depleted in Ile/Leu was found to be approximatively 105 mM whereas for lac-Ile, the maximum tested concentration of 951 mM was still soluble with a turbidity value below 5 NTU (FIG. 2). This indicates that Lac-Ile is at least 9 times more soluble than Ile in Cellvento® 4Feed depleted in Ile/Leu.

FIG. 2 shows the determination of the maximum solubility of Ile or Lac-Ile in a Cellvento® 4Feed formulation depleted in Ile and Leu (113 g/L, pH 7.0+/−0.2). A solution having a turbidity below 5 NTU is considered soluble.

The maximum solubility of Leu in Cellvento® 4Feed depleted in Ile and Leu was found to be approximatively 90 mM whereas for Lac-Leu, the maximum soluble concentration (with a turbidity value below 5 NTU) was approximatively 600 mM (FIG. 3). This indicates that Lac-Leu is 6.6 times more soluble than Leu in Cellvento® 4Feed depleted in Ile/Leu.

FIG. 3 shows the determination of the maximum solubility of Leu or Lac-Leu in a Cellvento® 4Feed formulation depleted in Ile and Leu (113 g/L, pH 7.0+/−0.2). A solution having a turbidity below 5 NTU is considered soluble.

Example 4: The Use of Lac-AA Enables the Concentration of Cell Culture Media Formulations at Neutral pH The maximum solubility of Cellvento® 4Feed (normal concentration 130 g/L) was determined by dissolving increasing amounts of feed dry powder media in water until precipitation was detected visually. For each condition, the feed was stirred for about 30 min, the pH was adjusted to 7.0+/−0.2 and the solution was stirred for another 10 min for equilibration. Osmolality and turbidity were measured, and pictures were taken (FIG. 4). The data indicate that already a 1.2× concentrate of this formulation (160 g/L) is not soluble since particles can be detected in suspension and the turbidity is largely above the limit of 5 NTU.

FIG. 4 shows the solubility limit of Cellvento® 4Feed at pH 7.0. Turbidity was measured using a turbidometer.

Since Ile and Leu have been identified as the first limiting amino acids for the concentration of the Cellvento® 4Feed formulation, a new backbone feed depleted in Ile and Leu was produced (Cellvento® 4Feed—Ile/Leu). The maximum concentration of this feed with supplementation with Lac-Leu and Lac-Ile was determined by dissolving increasing amounts of feed dry powder media+lactoyl derivatives in water until precipitation was detected visually. For each condition, the feed was stirred for about 30 min, the pH was adjusted to 7.0+/−0.2. and the solution was stirred for another 10 min for equilibration. Turbidity was measured and a limit of 5 NTU was considered soluble.

Results indicate that the maximum solubility of the Ile/Leu depleted Cellvento® 4Feed supplemented with Lac-Leu and Lac Ile was obtained between 189 g/L and 212 g/L (FIG. 5). Considering that Cellvento® 4Feed (containing Ile and Leu) has a concentration of 130 g/L, this represents an increase in concentration of approximatively 50% when Ile and Leu are replaced by Lac-Ile and Lac-Leu.

FIG. 5 shows the turbidity of solutions containing increasing amounts of Ile/Leu depleted 4Feed and supplemented with Lac-Leu and Lac-Ile derivatives (equimolar concentration compared to the free AA)

Example 5: Lac-Leu and Lac-Ile are Stable when Stored in Cellvento 4Feed-Ile/Leu for 3 Months at Either 4° C. or RT Protected from Light To monitor the stability of Lac-AA in the complex feed mixture, a targeted quantitative LC-MS method was developed. Serial dilutions of Lac-Leu and Lac-Ile in Cellvento® 4Feed—Ile/Leu pH 7.0 were performed from 100 mM to 100 μM to determine the linearity of the method. A 200-fold dilution in water was performed prior to LC-MS analysis. The method was developed on a UHPLC (Vanquish, Thermo Fisher) coupled with an ESI-Q-ToF mass spectrometer (Impact II, Bruker Daltonics).

Briefly, 1 μL of sample were loaded in 99.9% buffer A (20 mM ammonium formate/0.1% FA) onto a XSelect HSS T3 column (2.1×150 mm, 3.5 μm, Waters) thermostated at 40° C. with a flowrate of 300 μL/min and eluted with a multistep gradient of buffer B (100% methanol) presented in Table 2.

TABLE 2

Gradient of the chromatography method using the XSelect HSS T3 column

| | | Time (min) | | | | | | | | |
|---|---|---|---|---|---|---|---|---|---|---|
| | | 0 | 2 | 4 | 6 | 8 | 8.5 | 9.5 | 9.6 | 12 |
| Buffer | $A^1$ | 99.9 | 99.9 | 80 | 70 | 20 | 0 | 0 | 99.9 | 99.9 |
| (%) | $B^2$ | 0.1 | 0.1 | 20 | 30 | 80 | 100 | 100 | 0.1 | 0.1 |

[1] 20 mM ammonium formate/0.1% FA;
[2] 100% methanol

LC-MS analyses were performed using the Impact II mass spectrometer equipped with an ESI source (Bruker Daltonics). MS acquisition was performed in negative mode with end plate offset and capillary voltages set at 500 and 3500 V, respectively. Nebulizer and dry gas (250° C.) were set at 1.4 bar and 9.0 L/min, respectively. MS spectra were acquired over the m/z range 20-1000 with a scan rate of 5 Hz. Calibration was carried out using sodium formate solution injected at the start of the analysis.

The obtained standard curves for Lac-Leu and Lac Ile are presented in FIG. 6. A very good linearity was obtained for an injection between 10 pmol and 400 pmol on column (500 μM to 20 mM in the feed) whereas the linearity was not obtained for the range 2 pmol to 2 nmol on column (100 μM to 100 mM in the feed, not shown). Thus, Lac-AA quantification should be performed by injecting 10 to 400 pmol on column.

FIG. 6 shows the linearity obtained with the LC-MS method for Lac-Leu and Lac-Ile in Cellvento®4Feed—Ile/Leu after 200× dilution in water. A very good linearity was obtained in the range 10-400 pmol on column.

Using the method previously developed, the stability of Lac-Ile and Lac-Leu in Cellvento® 4Feed-Ile/Leu was monitored in samples stored at 4° C. and RT protected from light for 3 months. The stability of both lactoyl AA was very good at 4° C. and RT as shown in Figure indicating that Lac-Ile and Lac-Leu are stable if the feed formulation is stored for up to 3 months at either 4° C. or RT protected from light.

FIG. 7 shows the stability of Lac-Ile and Lac-Leu in Cellvento®4Feed—Ile/Leu as determined by LC-MS.

Example 6: Lac-Ile and Lac-Leu can Replace their Respective Amino Acids in the Feed. Cell Culture Results with a CHOK1GS Clone Producing an IgG1

For cell culture experiments, a CHOK1GS suspension cell line expressing a human IgG1, was used. Cells were cultivated in quadruplicate in Cellvento® 4CHO medium (Merck Darmstadt, Germany) using 50 mL spin tubes with a starting culture volume of 30 mL and a seeding density of $2\times10^5$ cells/mL.

Incubation was carried out at 37° C., 5% CO2, 80% humidity and an agitation of 320 rpm. The Lac-AA were added in the Feed (Cellvento® 4Feed depleted in Ile and leu) instead of their respective amino acids. The pH of all the feeds was neutral (pH 7.0+/−0.2). The positive control contained the normal amino acids whereas the negative control contained the feed depleted in the respective amino acid and without addition of Lac-AA. Feeding was carried out at days 3, 5, 7, 10, 12 and 14 at the following v/v ratios (3, 3, 6, 3, 3 and 3%). Glucose was quantified daily and adjusted to 6 g/L using a 400 g/L glucose solution. The experiment was repeated at least 3 times.

The viable cell density (VCD) and viability were evaluated with a Vi-CELL XR (Beckman Coulter, Fullerton, CA). Metabolite concentrations were monitored using a Cedex Bio HT (Roche Diagnostics, Mannheim, Germany) based on spectrophotometric and turbidometric methods. Quantification of amino acids was carried out via UPLC after derivatization with the AccQ·TagUltra® reagent kit. Derivatization, chromatography and data analysis were carried out following the supplier recommendations (Waters, Milford, MA).

When considering viable cell density (FIG. 8), the negative control for which the feed was depleted in Leu and Ile showed a rapid decrease in VCD after day 7 indicating that cells need both amino acids for efficient growth. The replacement of Ile by Lac-Ile had no effect on the peak VCD or overall VCD profile compared to the positive control whereas the replacement of Leu with Lac-Leu had a positive effect on the duration of the plateau phase since cells stayed at approximatively 15 million cells/mL for several days from day 10 to day 14.

FIG. 8 shows the VCD over a 17-days fed-batch process with either Lac-Leu or Lac-Ile replacing Leu and Ile respectively in the feed. Depleted Cellvento® 4Feed is the negative control and does not contain any Leu or Ile.

The IgG concentration obtained at day 14 was around 3 g/L for all conditions (FIG. 9) with a slight, but not significant higher titer for the conditions where Leu and Ile have been replaced with Lac-Leu and Lac-Ile respectively.

FIG. 9 shows the IgG produced over a 17-days fed-batch process with either Lac-Leu or Lac-Ile replacing Leu and Ile respectively in the feed.

Since the formation of free AA from Lac-AA is releasing lactate, this metabolite was monitored in the supernatant over the duration of the FB process (FIG. 10). In the conditions where Leu and Ile were replaced with Lac-Leu and Lac-Ile, respectively, a higher lactate concentration was observed after day 5, most likely resulting from the cleavage of the derivative. When calculating the area under the curve of lactate concentration, the overall increase in lactate was quantified. The replacement of Leu with Lac-Leu resulted in an increase of 20% of the free lactate whereas the replacement of Ile with Lac-Ile resulted in an increase of 37% which is quite similar to the increase in lactate observed in the negative control (36.5%).

FIG. 10 shows the lactate production during a 17-days fed-batch process with either Lac-Leu or Lac-Ile replacing Leu and Ile respectively in the feed.

The concentration of the amino acids was determined in spent media. In the condition in which Leu was replaced with Lac-Leu, the concentration of Leu in the spent medium (FIG. 11) decreased very rapidly until day 7 and increased again afterwards suggesting that the cleavage of the Lac-AA takes time, most probably depending on the release or activation of a specific enzyme (slow release technology similar to the previously developed phosphotyrosine release technology). In the condition where Ile was replaced with Lac-Ile, the overall leucine concentration over the fed-batch was moderately decreased indicating that other branched chain amino acids may be used instead of Ile, before efficient cleavage of the Lactoyl derivative.

When considering Ile in the spent medium (FIG. 12), a similar behavior as for Lac-Leu was detected. In the condition in which Ile was replaced with Lac-Ile, the concentration of Ile in the spent medium decreased very rapidly until day 7 and increased again afterwards suggesting that the cleavage of the Lac-AA takes time, most probably depending on the release or activation of a specific enzyme. In the condition where Leu was replaced with Lac-Leu, the Ile concentration was decreased after day 7 indicating that here too, other branched chain amino acids may be used instead of Leu.

FIG. 11: Leu quantification in the spent medium during a 17-days fed-batch process with either Lac-Leu or Lac-Ile replacing Leu and Ile respectively in the feed.

FIG. 12: Ile quantification in the spent medium during a 17-days fed-batch process with either Lac-Leu or Lac-Ile replacing Leu and Ile respectively in the feed.

The quality of the antibody produced in the control fed-batch process (with feed containing Ile and Leu) was compared to the quality of the antibody produced with feed depleted in either Leu and Ile and supplemented with either Lac-Leu or Lac-Ile.

The antibody was purified from the cell culture supernatant using protein A PhyTips® (PhyNexus Inc, San Jose, CA). Glycosylation patterns were analyzed by capillary gel electrophoresis with laser-induced fluorescence (CGE-LIF) after derivatization using the GlykoPrep®-plus Rapid N-Glycan Sample Preparation kit with 8-aminopyrene-1,3,6-trisulfonic acid trisodium (APTS) (Prozyme, Hayward, CA) according to the manufacturer's instructions. Briefly, the purified antibody was denatured and immobilized, and the glycans were released from the antibody by digestion with N-Glycanase® followed by labeling with APTS for 60 min at 50° C. After a cleaning step to remove the remaining APTS, the relative amounts of glycans were determined using the Pharmaceutical Analysis System CESI8000 Plus (Sciex, Washington, USA) with a LIF detector (Ex: 488 nm, Em: 520 nm). Separation was performed in a polyvinyl alcohol-coated capillary (total length: 50.2 cm, inner diameter: 50 μm) and filled with the carbohydrate separation buffer from the carbohydrate labeling kit (Beckman Coulter, Brea, USA). The capillary surface was first rinsed with separation buffer at 30 psi for 3 min. Inlet and outlet buffer vials were changed every 20 cycles. Samples were introduced by pressure injection at 0.5 psi for 12 s followed by a dipping step for 0.2 min to clean the capillary tips. Separation was finally performed at 20 kV for 20 min with a 0.17 min ramp applying reverse polarity. Peaks were identified according to their individual migration times and integrated according to the following parameters: peak width 0.05, threshold 10,000 and shoulder sensitivity 9,999.

Antibody aggregation and fragmentation were measured using size exclusion chromatography on an Water Acquity UPLC system using a TSKgel SuperSW3000 column (Tosoh Bioscience). The mobile phase was 0.05 M Sodium phosphate, 0.4 M Sodium perchlorate, pH 6.3 and the flow rate was 0.35 mL/min. The sample concentration was adjusted to 1.0 mg/mL after the IgG purification using the storage buffer and the detection was performed using the absorbance at 214 nm.

Charge variants were measured on a Capillary Electrophoresis CESI 8000 (Beckman Coulter/Sciex) using cIEF according to the manufacturer's instructions. The sample concentration was adjusted to a concentration of 1.5 mg/mL after the IgG purification using the storage buffer. Prior to the measurement, the samples were mixed with a master mix which contained different pH markers, a cathodic/anodic stabilizer, 3M Urea cIEF gel and Pharmalyte.

Results obtained for glycosylation (FIG. 13), high and low molecular weight species (FIG. 14) and charge variants (FIG. 15), indicate no difference between the control condition and the conditions where Ile and Leu were exchanged with Lac-Ile and Lac-Leu, indicating that the amino acid exchange has no impact on the three critical quality attributes of the IgG1 produced in this study.

Example 7: Confirmation of Lac-Leu and Lac-Ile Performance with a CHODG44 Clone Producing an IgG1

The applicability of the invention for different bioprocesses was demonstrated by performing fed-batch experiments with a CHODG44 clone. Results (FIG. 16, 17, 18) indicate a similar VCD and IgG titer for the Lac-Leu and Lac-Ile conditions compared to the control positive control. In contrast, the depleted Cellvento® 4Feed condition led to an early decrease in VCD and a significantly reduced titer after day 7. The spent media data show that for this cell line, no increase in lactate, from the cleavage of the Lac derivatives was detected. The explanation for this difference in behavior between CHOK1GS cells and this DG44 cell line is currently unknown. The Leu and Ile concentrations in the spent media (FIG. 19 and) decreased during the first day of the FB culture to finally increase again after D7. This behavior is similar to the behavior seen for CHOK1GS cells and indicate a slow release process of the free AA from the derivatives.

Figure 1:
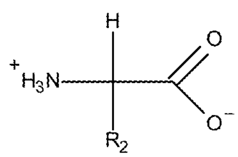
Figure 1:
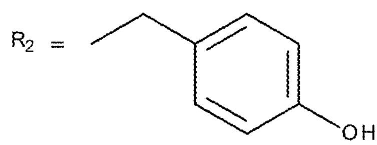
Figure 1:
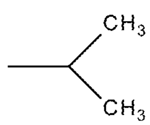
Figure 1:
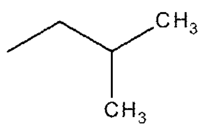
Figure 1:
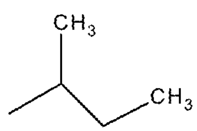
Figure 1:
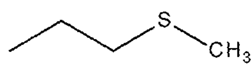
Figure 1:
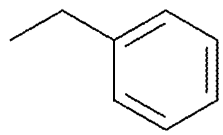
Figure 1:
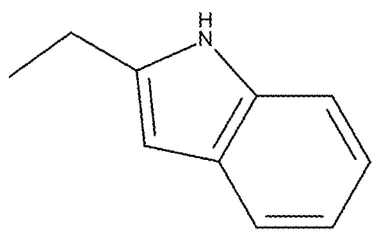
Figure 3:
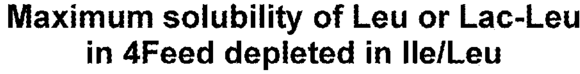
Figure 3:
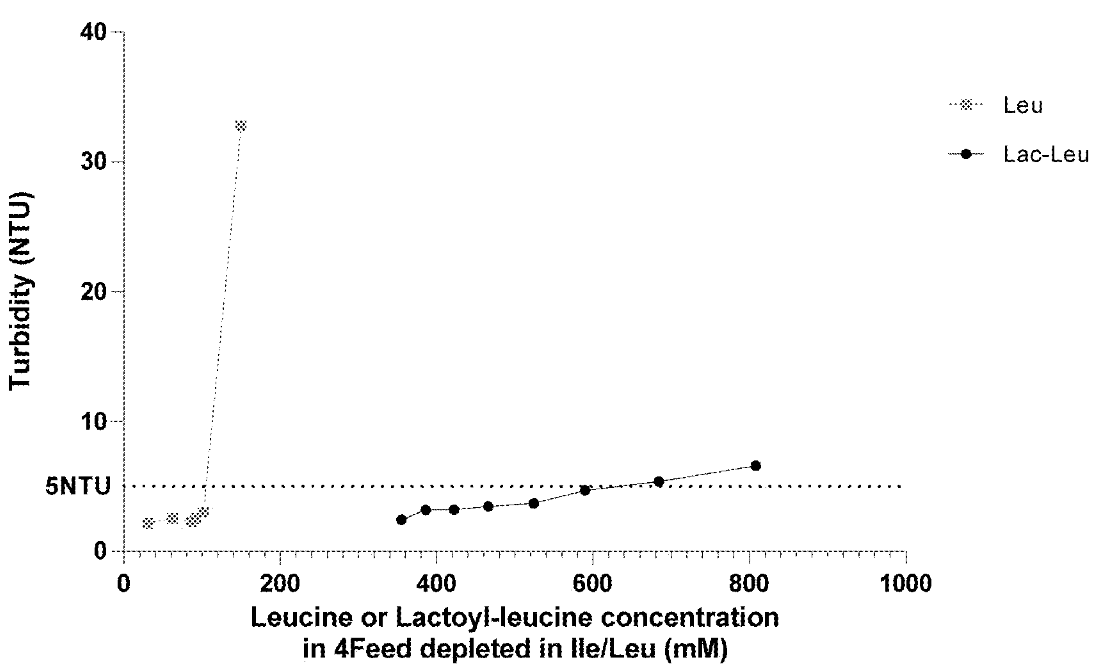
Figure 5:
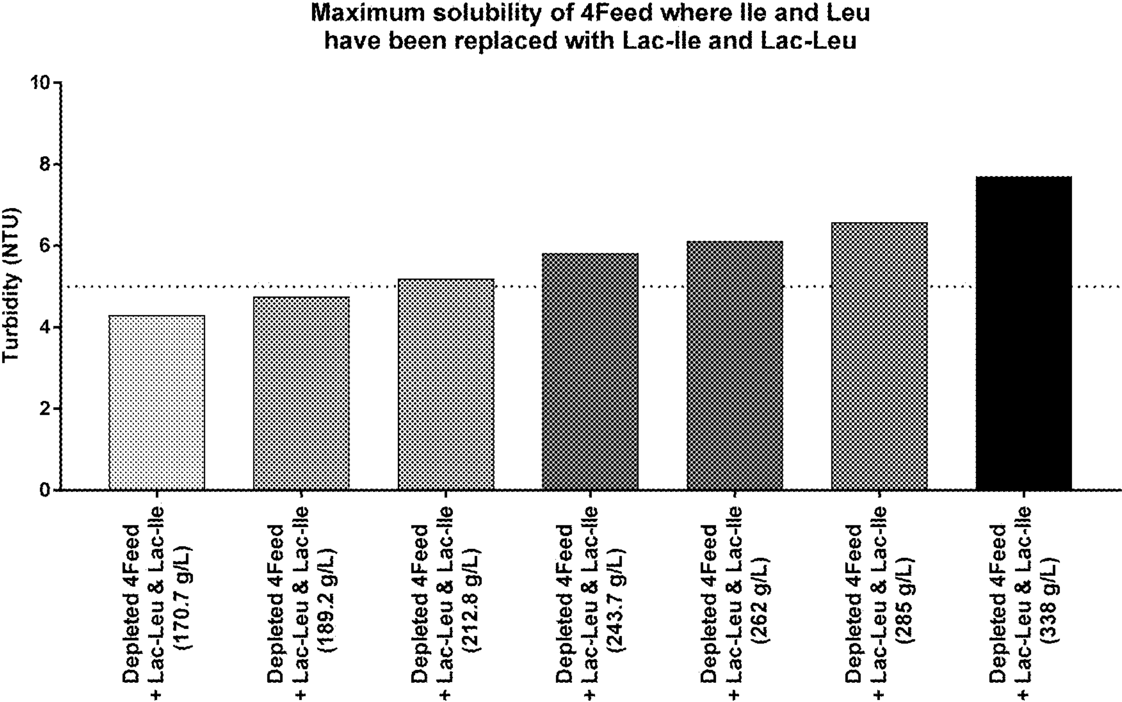
Figure 6:
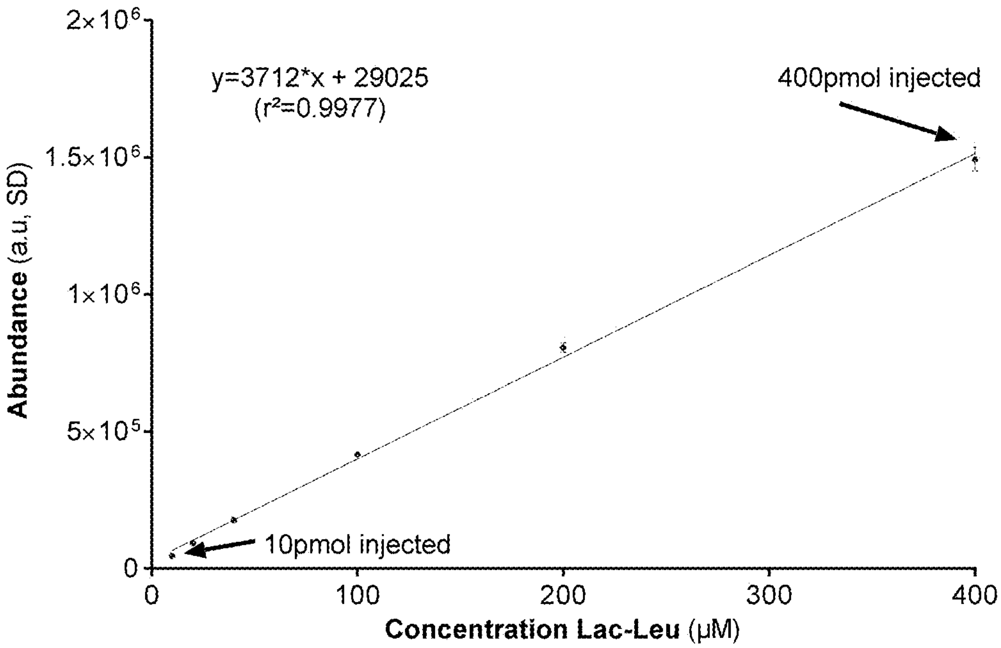
Figure 6:
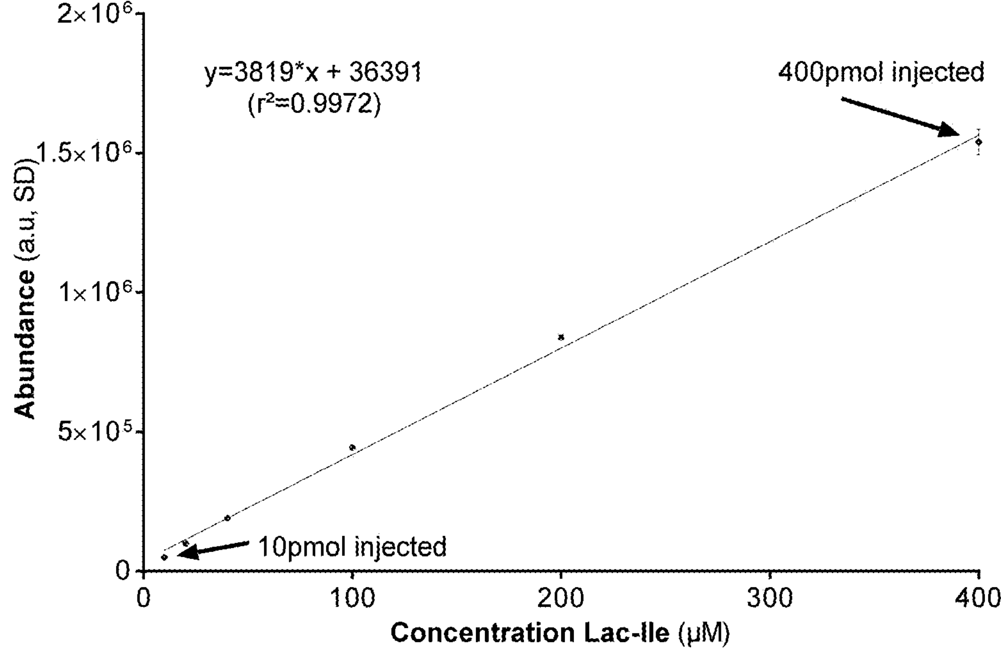
Figure 7:
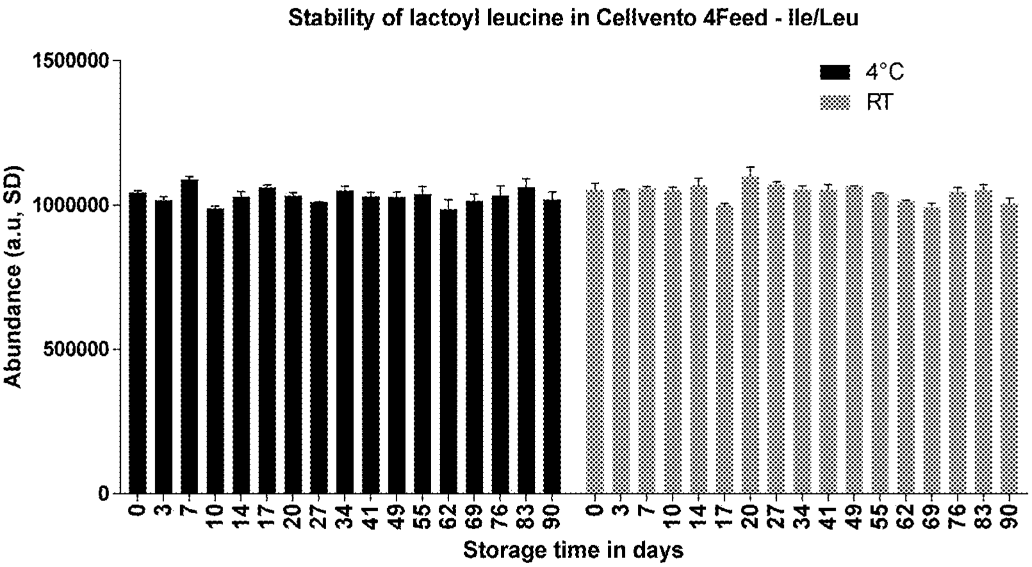
Figure 7:
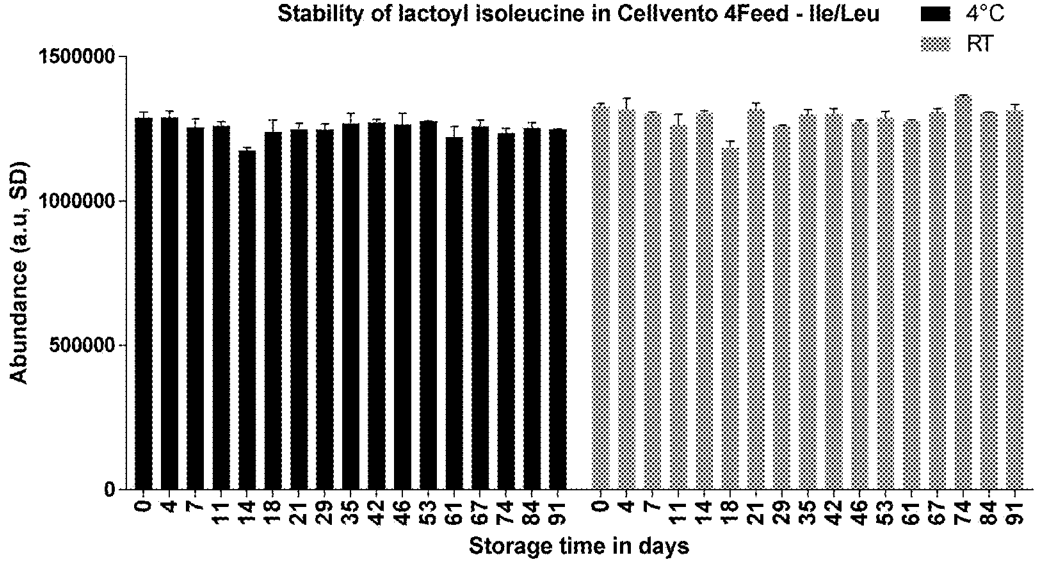
Figure 8:
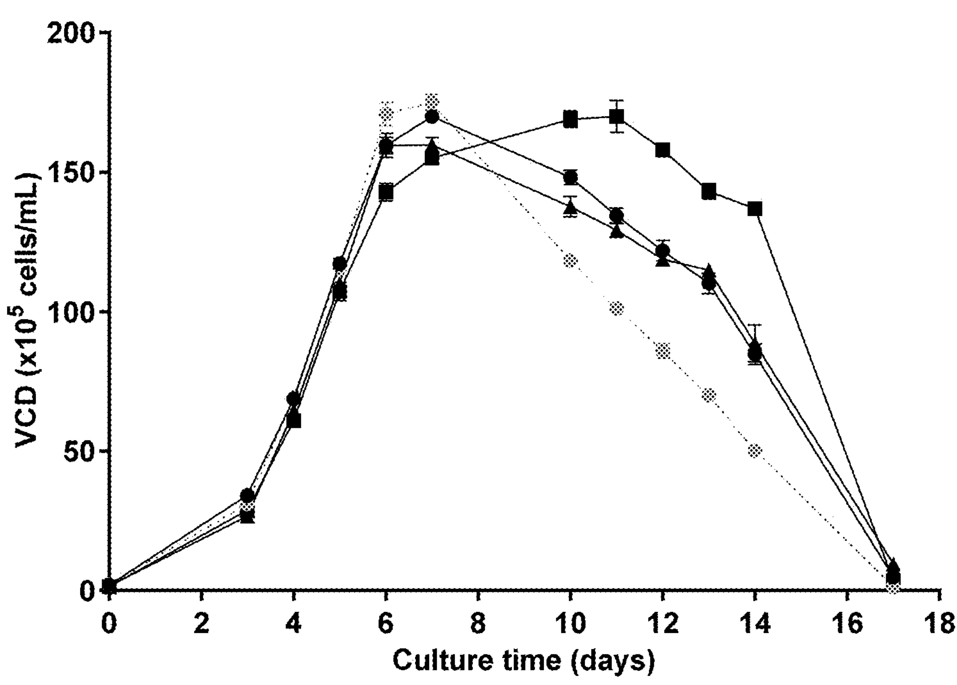
Figure 9:
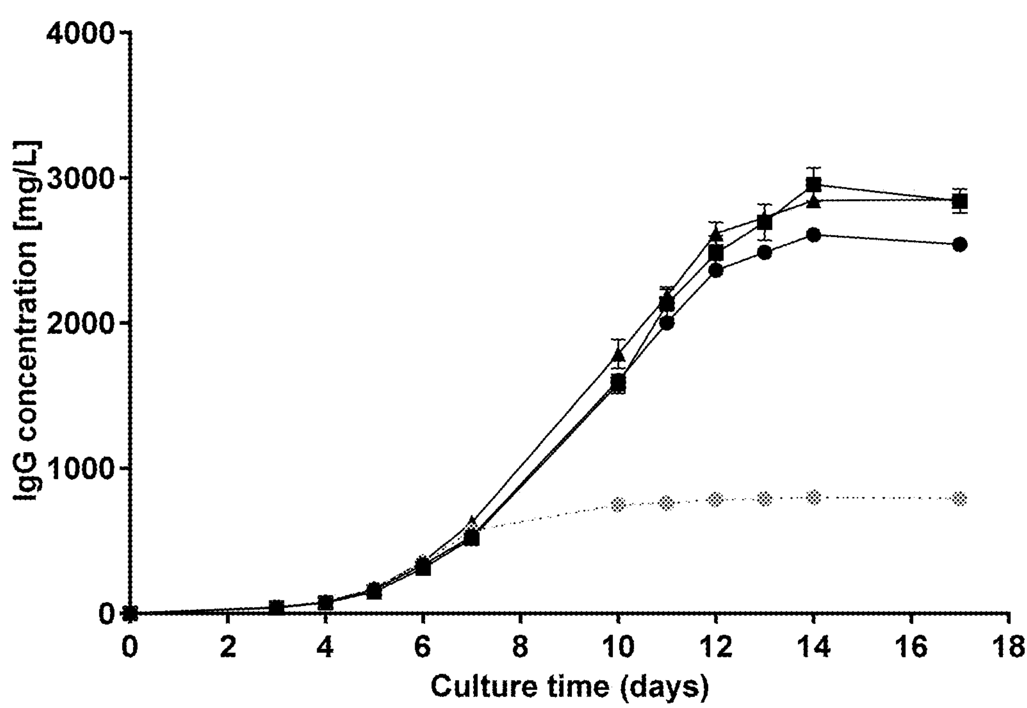
Figure 10:
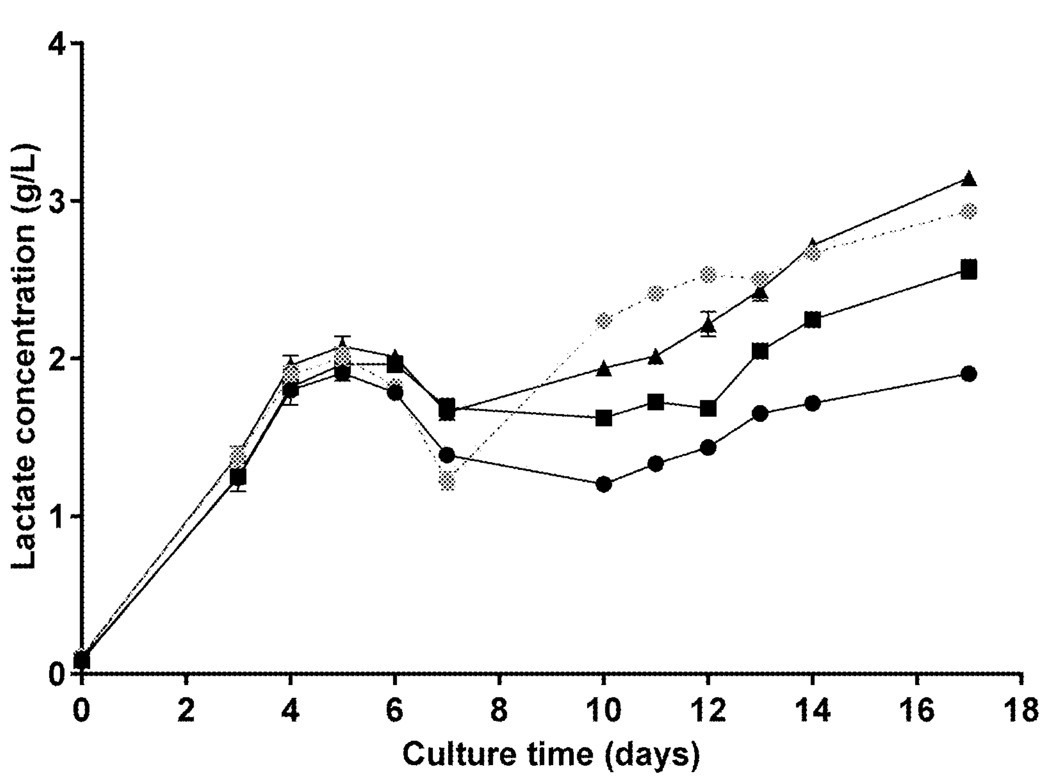
Figure 11:
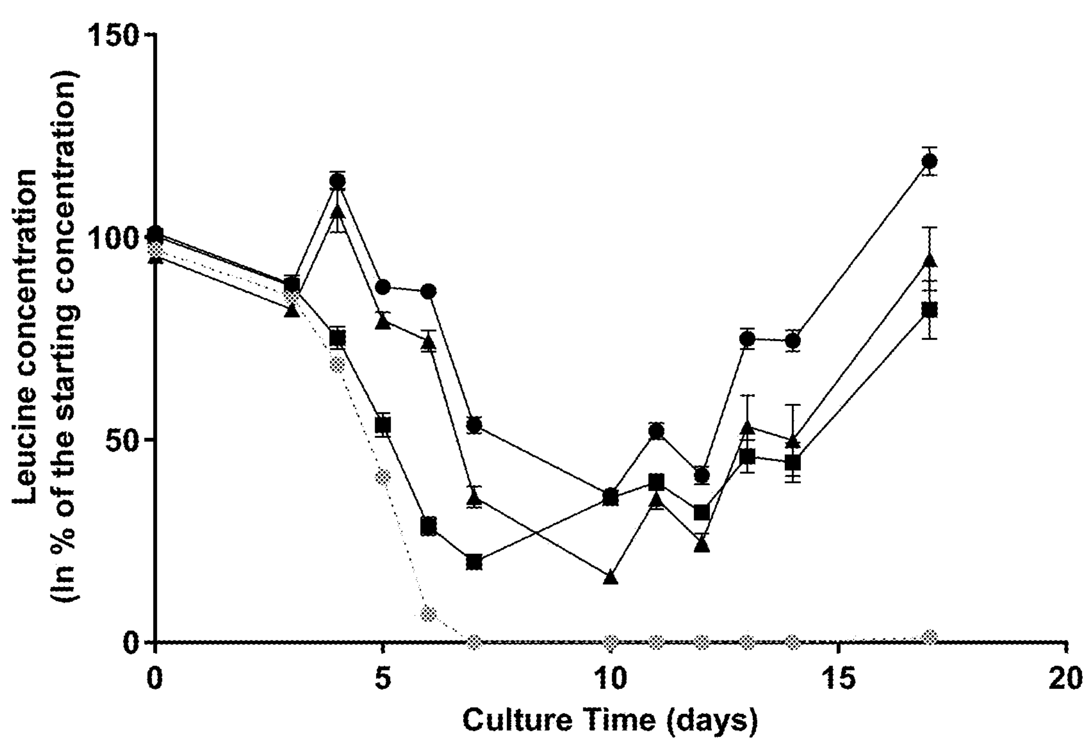
Figure 12:
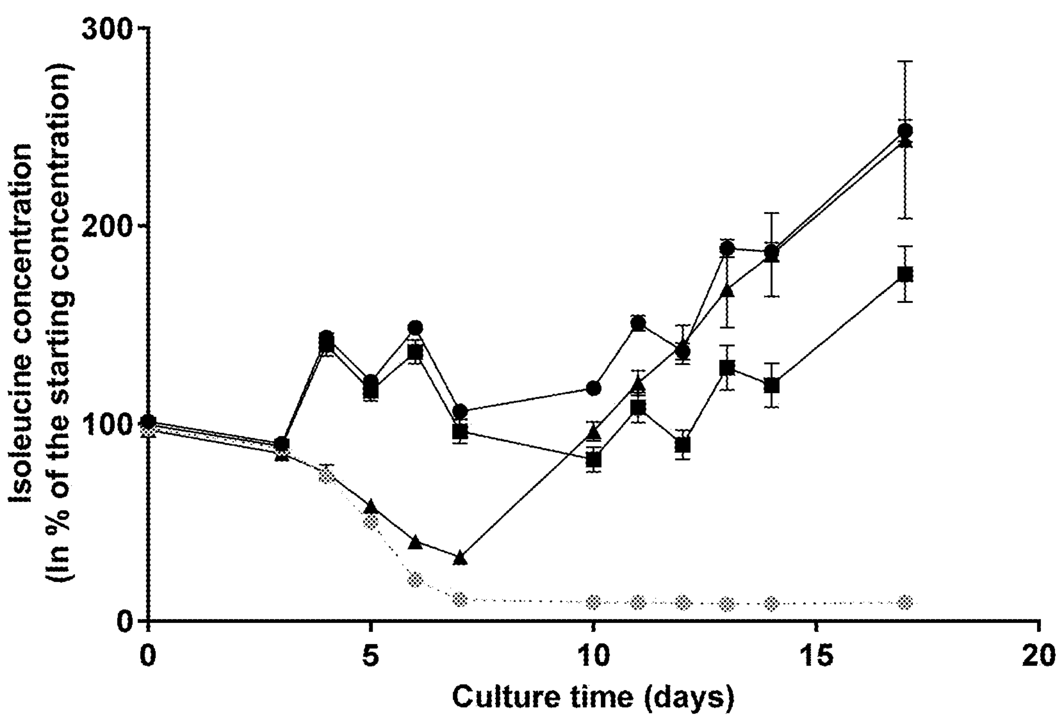
Figure 13:
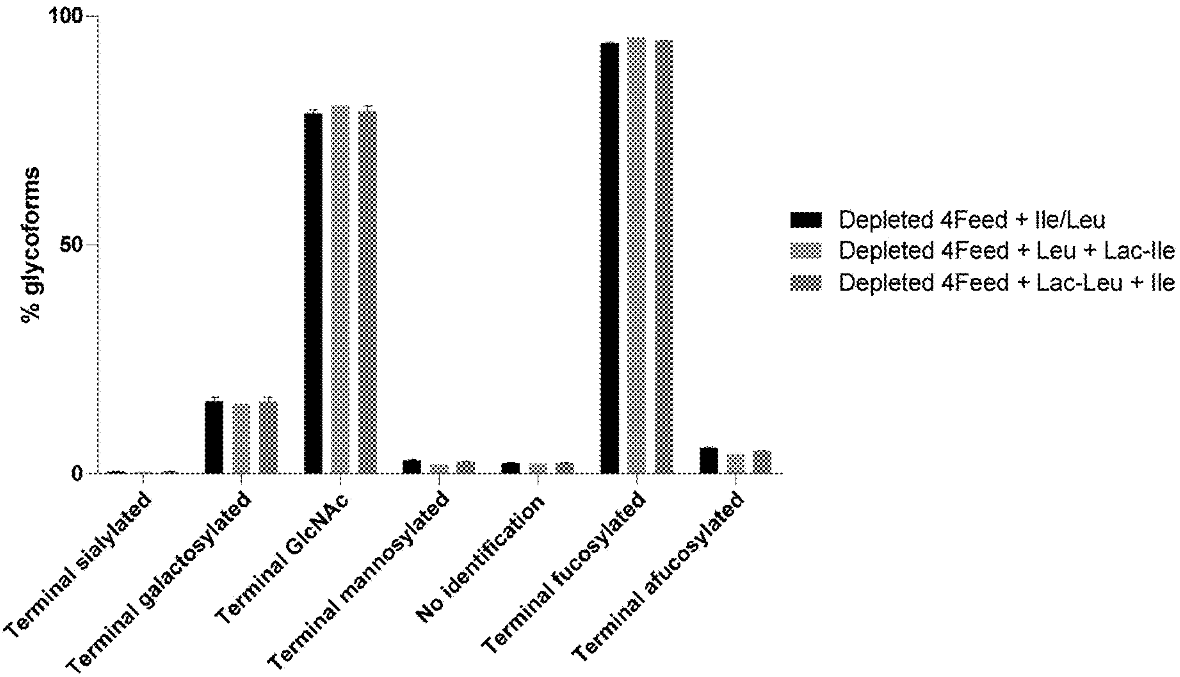
FIG. 13 shows the glycosylation of an IgG1 produced in the control process or in a process where a feed depleted in Ile/Leu and supplemented with either Lac-Leu or Lac-Ile was used. Glycoform distribution was determined using APTS labeling and CGE-LIF detection.
Figure 14:
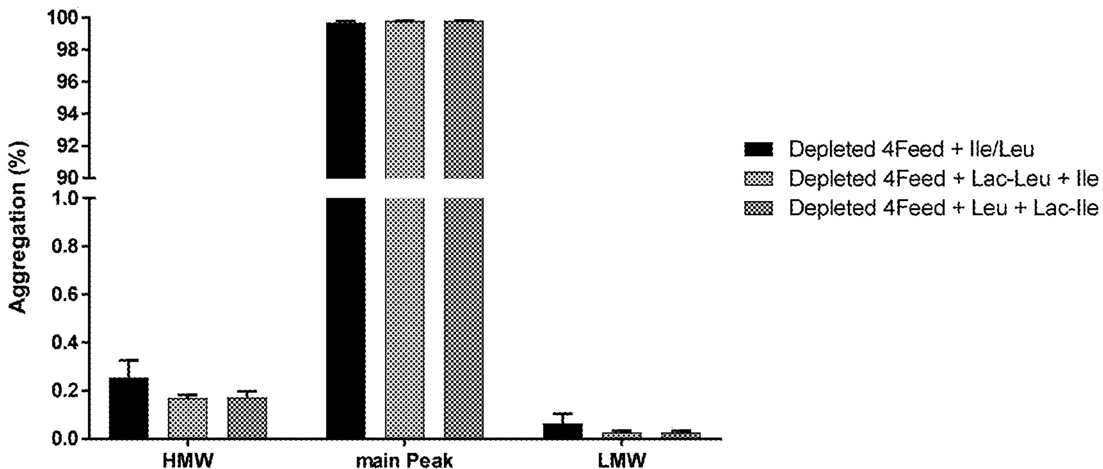
FIG. 14 shows the aggregation and fragmentation of an IgG1 produced in the control process or in a process where a feed depleted in Ile/Leu and supplemented with either Lac-Leu or Lac-Ile was used. High molecular weight (HMW) and low molecular weight species (LMW) were determined using size exclusion chromatography.
Figure 15:
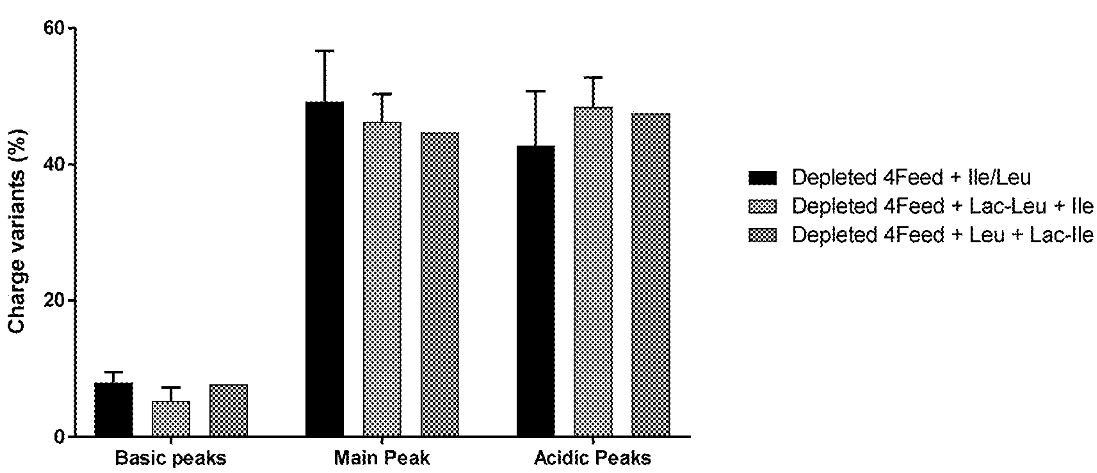
FIG. 15 shows the charge variants of an IgG1 produced in the control process or in a process where a feed depleted in Ile/Leu and supplemented with either Lac-Leu or Lac-Ile was used. Charge variant distribution was determined using cIEF on a Capillary Electrophoresis CESI 8000.
Figure 16:
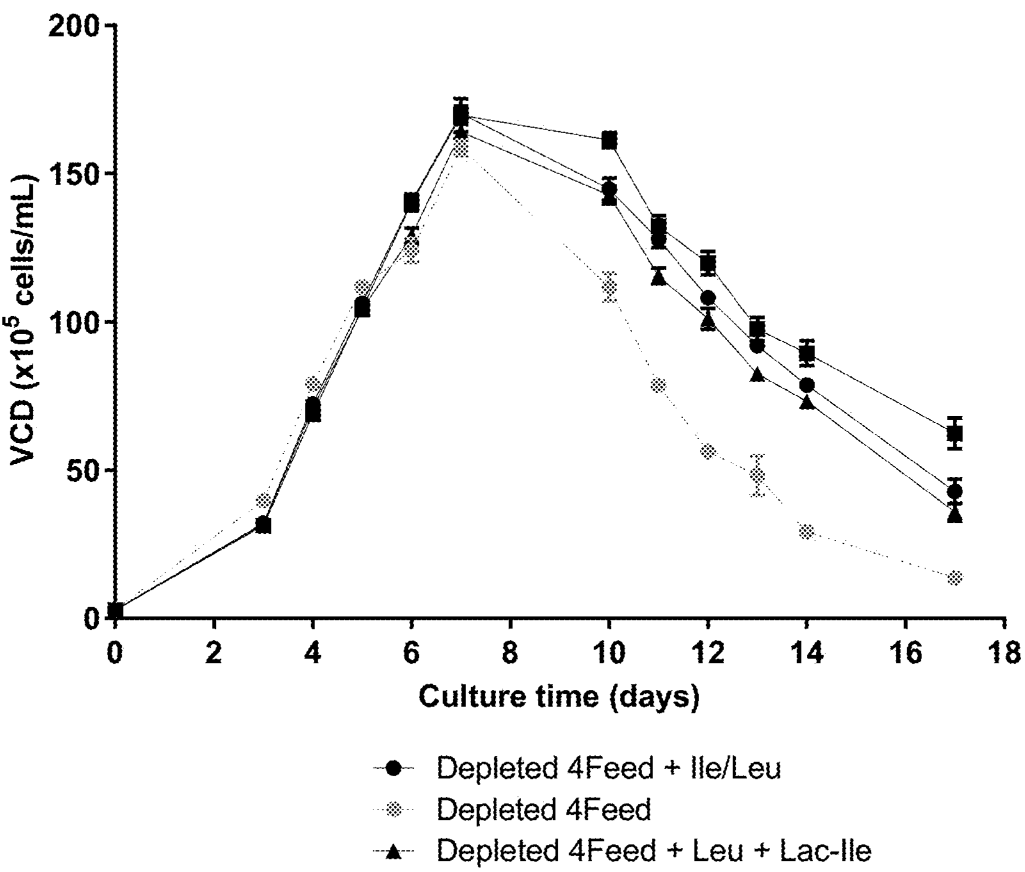
Figure 17:
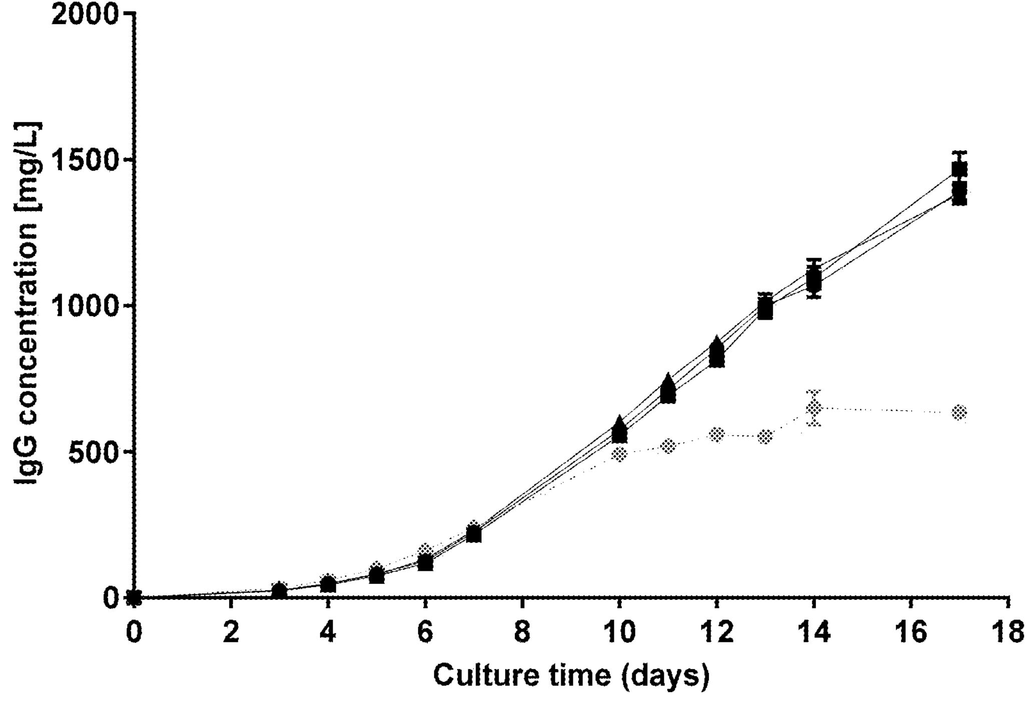
Figure 18:
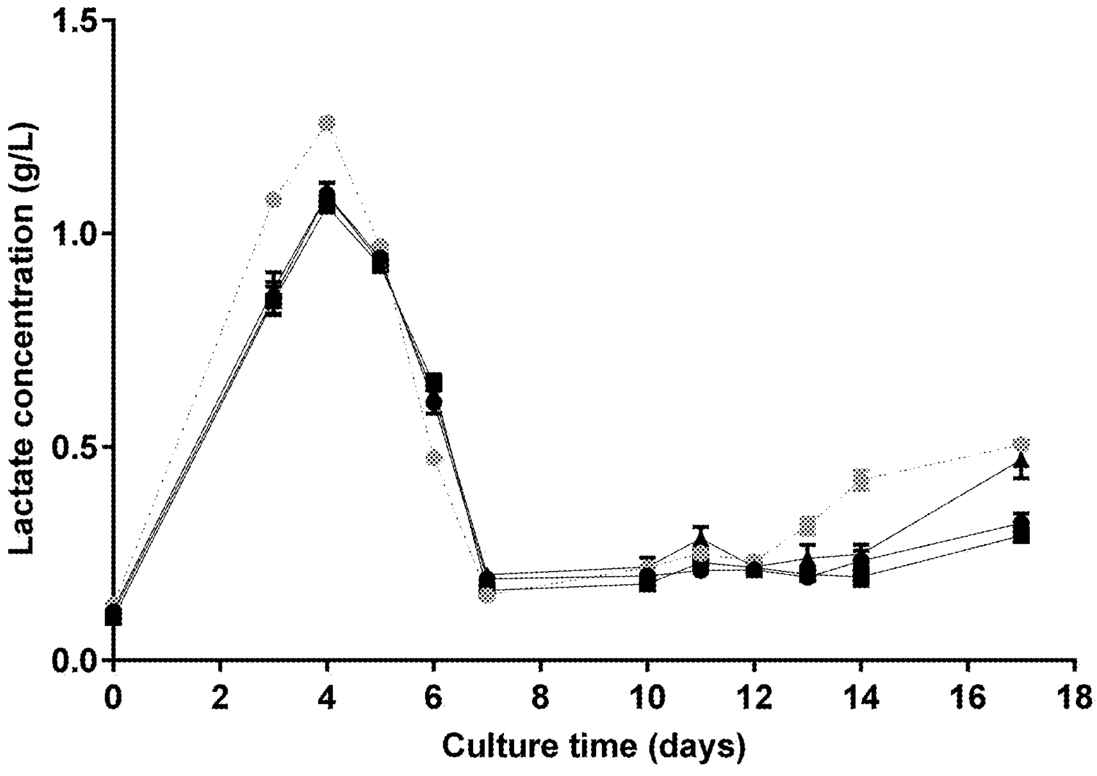

FIGS. 16, 17 and 18 show the performance of the Lac-Leu and Lac-Ile process compared to the controls for a CHODG44 cell line expressing an IgG1. Viable cell density (FIG. 16), IgG titer (FIG. 17), Lactate concentration in the spent medium (FIG. 18)

Figure 19:
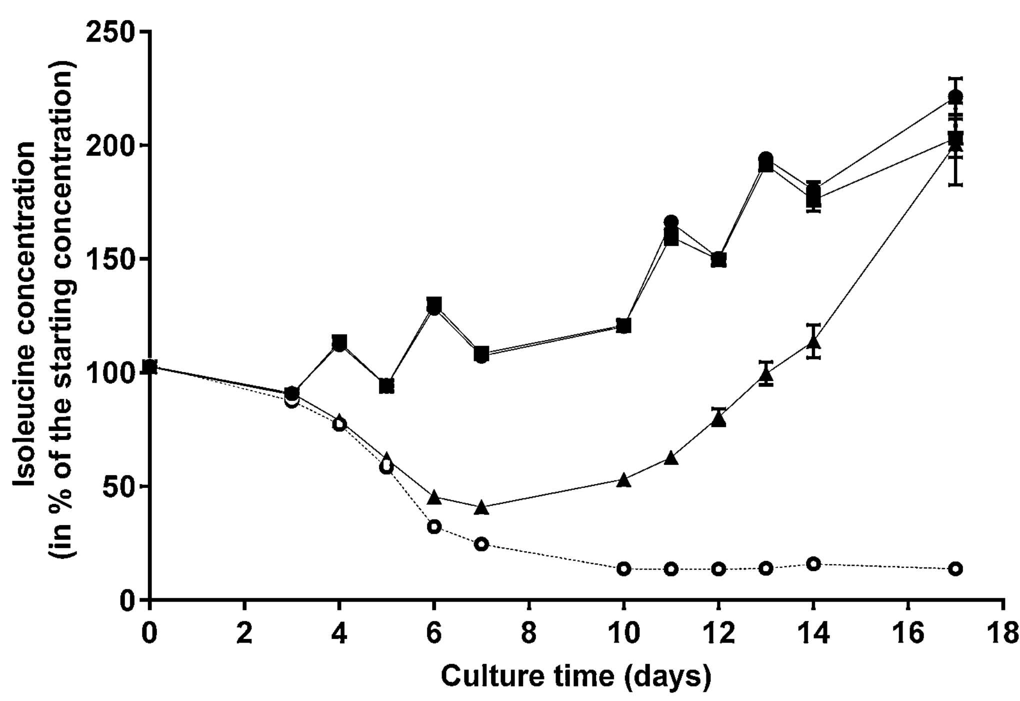
Figure 20:
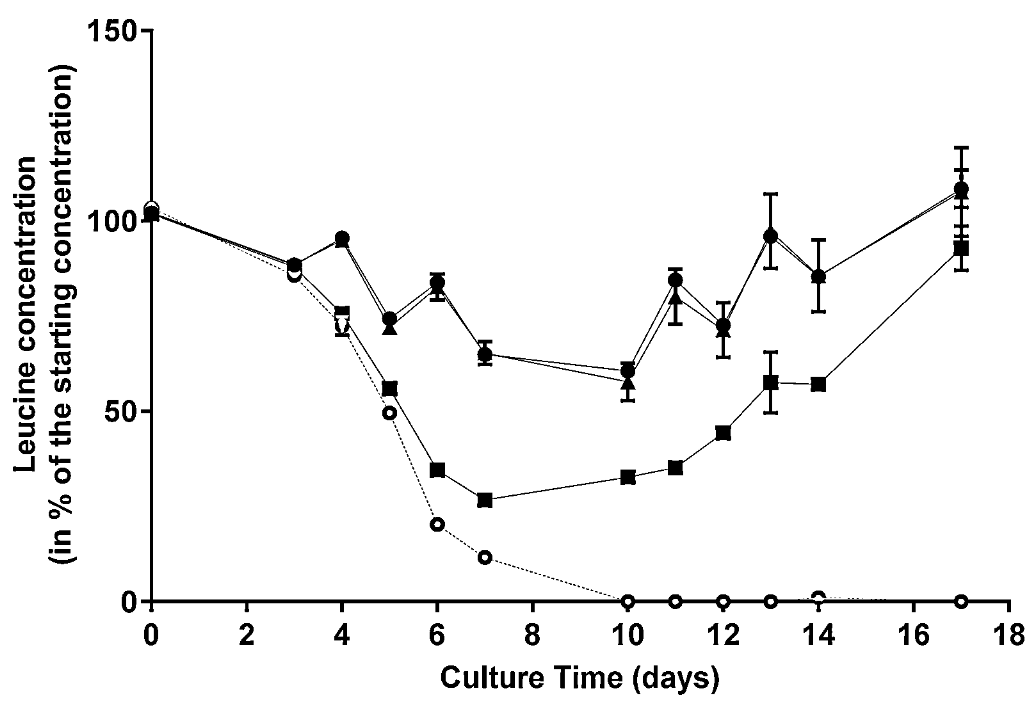

FIGS. 19 and 20 show the relative concentration of isoleucine (FIG. 19) and leucine (FIG. 20) in the spent medium in the Lac-Leu and Lac-Ile process (CHODG44 cells) compared to the normal process using unmodified Ile and Leu.

The invention claimed is:

1. A culture medium comprising at least one N-lactoyl-amino acid and/or salts thereof, wherein the culture medium is a chemically defined medium and is a dry powder medium, wherein the N-lactoyl-amino acid is selected from N-lactoyl-leucine, N-lactoyl-isoleucine, N-lactoyl-valine, N-lactoyl-phenylalanine, N-lactoyl-tyrosine and/or N-lactoyl-methionine.

2. The culture medium according to claim 1, characterized in that the cell culture medium comprises one or more of the components of formula I:

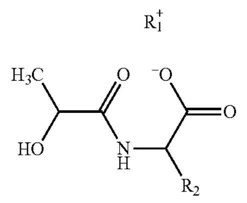

with $R_1^+$ being $H^+$ or $Na^+$, $K^+$, $Mg^{2+}$, $Ca^{2+}$, $Li^+$ and $R_2$ being the characteristic residue of the amino acid.

3. The culture medium according to claim 1, characterized in that the cell culture medium comprises the sodium salt of the one or more N-lactoyl amino acids.

4. The culture medium according to claim 1, characterized in that the cell culture medium comprises the one or more N-lactoyl amino acids and the corresponding amino acids and/or salts thereof.

5. The culture medium according to claim 2, characterized in that the medium comprises the one or more N-lactoyl amino acids and/or salts thereof but not the corresponding amino acids and/or salts thereof.

6. A method for producing a cell culture medium according to claim 1 by a) mixing one or more N-lactoyl-amino acids according to formula I with other components of the cell culture medium; and b) subjecting the mixture of step a) to milling.

7. A process for culturing prokaryotic or eukaryotic cells by a) providing a bioreactor, and providing a cell culture medium according to claim 2 and dissolving said cell culture medium in water or an aqueous buffer;

b) mixing the cells to be cultured with the cell culture medium; and c) incubating the mixture of step b).

8. The process according to claim 7, characterized in that the bioreactor is a perfusion bioreactor.

9. A process for culturing prokaryotic or eukaryotic cells in a bioreactor by (a) filling the cells into the bioreactor;

(b) incubating the cells in the bioreactor; and (c) adding a medium to the bioreactor, continuously over the whole time or once or several times within the cells incubation time;

whereby the medium is prepared by providing a cell culture medium according to claim 1 and dissolving said cell culture medium in water or an aqueous buffer.

10. The process according to claim 9, characterized in that the N-lactoyl amino acid is N-lactoyl leucine and/or N-lactoyl isoleucine and/or salts thereof.

* * * * *